United States Patent
Beitz et al.

(10) Patent No.: US 11,365,495 B2
(45) Date of Patent: Jun. 21, 2022

(54) PROCESS FOR MAKING FLUID-ENTANGLED LAMINATE WEBS WITH HOLLOW PROJECTIONS AND APERTURES

(71) Applicant: Kimberly-Clark Worldwide, Inc., Neenah, WI (US)

(72) Inventors: Mark J. Beitz, Appleton, WI (US); Stacy E. Evenson, Neenah, WI (US); Andrew T. Hammond, Grand Chute, WI (US); Sarah Kleuskens, Neenah, WI (US); Amy Q. Feng, Neenah, WI (US); Patrick D. Abney, Menasha, WI (US); Kevin G. Dolan, Appleton, WI (US); Robert M. Hill, Neenah, WI (US); Kroy D. Johnson, Neenah, WI (US); Niall Finn, Lethbridge (AU); Andy Butler, Albert Park (AU); Danielle Kirby, Putney (AU); Phil Penaia, Altona (AU)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/487,185

(22) PCT Filed: Feb. 28, 2017

(86) PCT No.: PCT/US2017/019864
§ 371 (c)(1),
(2) Date: Aug. 20, 2019

(87) PCT Pub. No.: WO2018/160161
PCT Pub. Date: Sep. 7, 2018

(65) Prior Publication Data
US 2020/0378044 A1    Dec. 3, 2020

(51) Int. Cl.
*D04H 1/495*    (2012.01)
*A61F 13/15*    (2006.01)
*D04H 1/498*    (2012.01)

(52) U.S. Cl.
CPC ....... *D04H 1/495* (2013.01); *A61F 13/15577* (2013.01); *D04H 1/498* (2013.01); *A61F 2013/15983* (2013.01)

(58) Field of Classification Search
CPC ........ D04H 1/492; D04H 1/495; D04H 1/498; D04H 5/03; A61F 13/15577; A61F 2013/15983
(Continued)

(56) References Cited

U.S. PATENT DOCUMENTS

| 2,862,251 | A | * | 12/1958 | Kalwaites | D21F 11/006 |
| | | | | | 264/119 |
| 3,081,515 | A | * | 3/1963 | Griswold | D04H 1/736 |
| | | | | | 428/131 |

(Continued)

FOREIGN PATENT DOCUMENTS

| CN | 1049388 A | 2/1991 |
| CN | 1134475 A | 10/1996 |

(Continued)

OTHER PUBLICATIONS

Beaumont, Donald F. and Dr. Kenneth R. Randall, "Rotary Hydraulic Entanglement of Nonwovens," Nonwovens World, vol. 1, No. 3, Nov. 1986, pp. 76-80, reprinted from INSIGHT 86 International Advanced Forming/Bonding Conference.

(Continued)

*Primary Examiner* — Khoa D Huynh
*Assistant Examiner* — Uyen T Nguyen
(74) *Attorney, Agent, or Firm* — Kimberly-Clark Worldwide, Inc.

(57) ABSTRACT

The present invention is directed to a process and apparatus for formation of a fluid-entangled laminate web. The lami- (Continued)

nate web includes a support layer and a nonwoven projection web having a plurality of projections which are preferably hollow. The laminate web also includes a plurality of apertures interspersed with the projections. As a result of the fluid-entangling process, entangling fluid is directed through the support layer and into the projection web which is situated on a forming surface. The force of the entangling fluid causes the two layers to be joined to one another and the fluid causes a portion of the fibers in the projection web to be forced into openings present in a forming surface thereby forming the hollow projections. The force of the entangling fluid also causes the fibers of the two layers to be moved around protrusions present in the forming surface thereby forming the apertures.

19 Claims, 7 Drawing Sheets

(58) Field of Classification Search
USPC .......................................... 28/104, 105, 106
See application file for complete search history.

(56) References Cited

U.S. PATENT DOCUMENTS

| | | | |
|---|---|---|---|
| 3,485,706 A | 12/1969 | James | |
| 3,717,532 A | 2/1973 | Kamp | |
| 3,766,922 A | 10/1973 | Krusko | |
| 3,855,046 A | 12/1974 | Hansen et al. | |
| 3,917,785 A * | 11/1975 | Kalwaites | D04H 5/03 |
| | | | 264/108 |
| 4,041,951 A | 8/1977 | Sanford | |
| 4,202,868 A | 5/1980 | Hayashi et al. | |
| 4,333,979 A | 6/1982 | Sciaraffa et al. | |
| 4,609,518 A * | 9/1986 | Curro | A61F 13/15577 |
| | | | 264/504 |
| 4,614,679 A | 9/1986 | Farrington et al. | |
| 4,673,402 A | 6/1987 | Weisman et al. | |
| 4,704,112 A | 11/1987 | Suzuki et al. | |
| 4,718,152 A | 1/1988 | Suzuki et al. | |
| 4,741,941 A | 5/1988 | Englebert et al. | |
| 4,780,352 A | 10/1988 | Palumbo | |
| 4,781,710 A | 11/1988 | Megison et al. | |
| 4,805,275 A | 2/1989 | Suzuki et al. | |
| 4,846,821 A * | 7/1989 | Lyons | A61F 13/51476 |
| | | | 604/369 |
| 4,868,958 A * | 9/1989 | Suzuki | D04H 18/04 |
| | | | 28/104 |
| 4,879,170 A | 11/1989 | Radwanski et al. | |
| 4,931,355 A | 6/1990 | Radwanski et al. | |
| 4,939,016 A | 7/1990 | Radwanski et al. | |
| 4,950,531 A | 8/1990 | Radwanski et al. | |
| 4,970,104 A | 11/1990 | Radwanski | |
| 5,019,062 A | 5/1991 | Ryan et al. | |
| 5,098,764 A | 3/1992 | Bassett et al. | |
| 5,137,600 A | 8/1992 | Barnes et al. | |
| 5,144,729 A | 9/1992 | Austin et al. | |
| 5,180,620 A | 1/1993 | Mende | |
| 5,242,632 A | 9/1993 | Mende | |
| 5,244,711 A | 9/1993 | Drelich et al. | |
| 5,301,401 A | 4/1994 | Suzuki et al. | |
| 5,369,858 A | 12/1994 | Gilmore et al. | |
| 5,389,202 A | 2/1995 | Everhart et al. | |
| 5,407,439 A | 4/1995 | Goulait | |
| 5,415,640 A | 5/1995 | Kirby et al. | |
| 5,500,270 A | 3/1996 | Langdon et al. | |
| 5,505,720 A | 4/1996 | Walters et al. | |
| 5,514,120 A | 5/1996 | Johnston et al. | |
| 5,527,300 A | 6/1996 | Sauer | |
| 5,575,874 A | 11/1996 | Griesbach et al. | |
| 5,614,281 A | 3/1997 | Jackson et al. | |
| 5,624,427 A | 4/1997 | Bergman et al. | |
| 5,656,232 A | 8/1997 | Takai et al. | |
| 5,785,697 A * | 7/1998 | Trombetta | A61F 13/532 |
| | | | 604/378 |
| 5,830,202 A | 11/1998 | Bogdanski et al. | |
| 5,858,515 A | 1/1999 | Stokes et al. | |
| 5,888,607 A | 3/1999 | Seth et al. | |
| 5,906,879 A | 5/1999 | Huntoon et al. | |
| 5,928,212 A | 7/1999 | Kline et al. | |
| 5,962,112 A | 10/1999 | Haynes et al. | |
| 5,990,377 A | 11/1999 | Chen et al. | |
| 5,997,981 A | 12/1999 | McCormack et al. | |
| 6,022,818 A | 2/2000 | Welchel et al. | |
| 6,176,954 B1 | 1/2001 | Tsuji et al. | |
| 6,192,556 B1 | 2/2001 | Kikko et al. | |
| 6,222,092 B1 | 4/2001 | Hansen et al. | |
| 6,228,216 B1 | 5/2001 | Lindsay et al. | |
| 6,241,714 B1 | 6/2001 | Raidel et al. | |
| 6,242,074 B1 | 6/2001 | Thomas | |
| 6,290,685 B1 | 9/2001 | Insley et al. | |
| 6,290,979 B1 | 9/2001 | Roe et al. | |
| 6,291,050 B1 | 9/2001 | Cree et al. | |
| 6,314,627 B1 * | 11/2001 | Ngai | B32B 5/26 |
| | | | 28/104 |
| 6,316,687 B1 | 11/2001 | Davis et al. | |
| 6,319,455 B1 | 11/2001 | Kauschke et al. | |
| 6,331,268 B1 | 12/2001 | Kauschke et al. | |
| 6,331,345 B1 | 12/2001 | Kauschke et al. | |
| 6,395,957 B1 | 5/2002 | Chen et al. | |
| 6,413,344 B2 | 7/2002 | Bodaghi | |
| 6,417,427 B1 | 7/2002 | Roxendal et al. | |
| 6,436,512 B1 | 8/2002 | Kauschke et al. | |
| 6,440,114 B1 | 8/2002 | Bast et al. | |
| 6,468,626 B1 | 10/2002 | Takai et al. | |
| 6,488,801 B1 | 12/2002 | Bodaghi et al. | |
| 6,502,288 B2 | 1/2003 | Black et al. | |
| 6,521,555 B1 | 2/2003 | Bodaghi et al. | |
| 6,610,173 B1 | 8/2003 | Lindsay et al. | |
| 6,610,904 B1 | 8/2003 | Thomas et al. | |
| 6,660,362 B1 | 12/2003 | Lindsay et al. | |
| 6,689,242 B2 | 2/2004 | Bodaghi | |
| 6,725,512 B2 | 4/2004 | Carter | |
| 6,733,610 B2 | 5/2004 | Mizutani et al. | |
| 6,735,832 B1 | 5/2004 | Putnam et al. | |
| 6,802,932 B2 | 10/2004 | Kudo et al. | |
| 6,822,134 B1 | 11/2004 | Stiehl et al. | |
| 6,838,591 B2 | 1/2005 | Waksmundzki et al. | |
| 6,888,046 B2 | 5/2005 | Toyoshima et al. | |
| 6,911,573 B2 | 6/2005 | Chen et al. | |
| 6,911,574 B1 | 6/2005 | Mizutani | |
| 6,936,038 B2 | 8/2005 | Tears et al. | |
| 6,936,333 B2 | 8/2005 | Shizuno et al. | |
| 6,955,847 B1 | 10/2005 | Itou et al. | |
| 6,998,017 B2 | 2/2006 | Lindsay et al. | |
| 7,105,716 B2 | 9/2006 | Baratian et al. | |
| 7,132,585 B2 | 11/2006 | Kudo et al. | |
| 7,172,801 B2 | 2/2007 | Hoying et al. | |
| 7,175,613 B2 | 2/2007 | Sugiyama et al. | |
| 7,194,788 B2 | 3/2007 | Clark et al. | |
| 7,267,860 B2 | 9/2007 | Toyoshima et al. | |
| 7,294,387 B2 | 11/2007 | Wildeman | |
| 7,303,805 B2 | 12/2007 | Seth et al. | |
| 7,303,808 B2 | 12/2007 | Taneichi et al. | |
| 7,410,683 B2 | 8/2008 | Curro et al. | |
| 7,455,800 B2 * | 11/2008 | Ferencz | D04H 3/11 |
| | | | 264/103 |
| 7,468,114 B2 | 12/2008 | Sato et al. | |
| 7,507,463 B2 | 3/2009 | Noda et al. | |
| 7,518,032 B2 | 4/2009 | Seyler | |
| 7,534,928 B2 | 5/2009 | Sakamoto et al. | |
| 7,547,469 B2 | 6/2009 | Provost et al. | |
| 7,553,532 B2 | 6/2009 | Turner et al. | |
| 7,553,535 B2 | 6/2009 | Noda et al. | |
| 7,569,264 B2 | 8/2009 | Toyoshima et al. | |
| 7,589,251 B2 | 9/2009 | Roe | |
| 7,632,258 B2 | 12/2009 | Misek et al. | |
| 7,648,752 B2 | 1/2010 | Hoying et al. | |
| 7,662,462 B2 | 2/2010 | Noda et al. | |
| 7,678,442 B2 | 3/2010 | Casey et al. | |
| 7,682,686 B2 | 3/2010 | Curro et al. | |
| 7,686,921 B2 | 3/2010 | Hamed et al. | |

(56) References Cited

U.S. PATENT DOCUMENTS

| | | |
|---|---|---|
| 7,687,681 B2 | 3/2010 | Di Luccio et al. |
| 7,717,150 B2 | 5/2010 | Manabe et al. |
| 7,718,243 B2 | 5/2010 | Curro et al. |
| 7,718,249 B2 * | 5/2010 | Russell ............... A61F 13/5323 428/188 |
| 7,815,995 B2 * | 10/2010 | Clark ..................... D04H 5/03 428/152 |
| 7,829,173 B2 | 11/2010 | Turner et al. |
| 7,838,099 B2 * | 11/2010 | Curro ................... D04H 11/00 428/96 |
| 7,851,047 B2 | 12/2010 | Sato et al. |
| 7,855,314 B2 | 12/2010 | Hanao et al. |
| 7,884,259 B2 | 2/2011 | Hanao et al. |
| 7,897,240 B2 | 3/2011 | Noda et al. |
| 7,935,861 B2 | 5/2011 | Suzuki |
| 7,942,992 B2 | 5/2011 | Saka et al. |
| 7,954,213 B2 | 6/2011 | Mizutani et al. |
| 7,955,549 B2 | 6/2011 | Noda et al. |
| 7,972,985 B2 | 7/2011 | Hirose et al. |
| 7,981,822 B2 | 7/2011 | Lester, Jr. et al. |
| 7,993,317 B2 | 8/2011 | Hammons et al. |
| 8,022,267 B2 * | 9/2011 | Hellstrom ............. D04H 1/492 604/367 |
| 8,075,977 B2 | 12/2011 | Curro et al. |
| 8,105,526 B2 * | 1/2012 | Stone ..................... B29C 33/00 264/400 |
| 8,143,177 B2 | 3/2012 | Noda et al. |
| 8,153,225 B2 | 4/2012 | Turner et al. |
| 8,183,431 B2 | 5/2012 | Noda et al. |
| 8,206,628 B2 | 6/2012 | Stone et al. |
| 8,235,959 B2 | 8/2012 | Ponomarenko et al. |
| 8,273,942 B2 | 9/2012 | Roe |
| 8,304,600 B2 | 11/2012 | Noda et al. |
| 8,393,374 B2 | 3/2013 | Sato et al. |
| 8,450,557 B2 | 5/2013 | Nishitani et al. |
| 8,575,418 B2 | 11/2013 | Gabrielii et al. |
| 8,617,449 B2 | 12/2013 | Baker et al. |
| 8,722,173 B2 | 5/2014 | Oba et al. |
| 8,748,692 B2 | 6/2014 | Suzuki |
| 8,765,250 B2 | 7/2014 | Seyler et al. |
| 8,784,972 B2 | 7/2014 | Sato et al. |
| 8,865,965 B2 | 10/2014 | Sato et al. |
| 9,327,473 B2 | 5/2016 | Finn et al. |
| 9,445,951 B2 | 9/2016 | Moberg-Alehammar et al. |
| 9,474,660 B2 | 10/2016 | Kirby et al. |
| 9,480,608 B2 | 11/2016 | Kirby et al. |
| 9,480,609 B2 * | 11/2016 | Kirby ................ A61F 13/51104 |
| 9,789,009 B2 | 10/2017 | Joseph |
| 9,987,175 B2 | 6/2018 | Butler et al. |
| 10,070,999 B2 | 9/2018 | Faulks et al. |
| 10,285,874 B2 | 5/2019 | Tally et al. |
| 10,470,947 B2 | 11/2019 | Kirby et al. |
| 10,478,354 B2 | 11/2019 | Kirby et al. |
| 2001/0027302 A1 | 10/2001 | Glaug et al. |
| 2002/0034914 A1 * | 3/2002 | De Leon ............... D04H 1/49 442/384 |
| 2002/0132544 A1 | 9/2002 | Takagaki |
| 2002/0143311 A1 | 10/2002 | Brisebois |
| 2003/0003832 A1 | 1/2003 | Childs et al. |
| 2003/0008108 A1 | 1/2003 | Shizuno et al. |
| 2003/0036741 A1 | 2/2003 | Abba et al. |
| 2003/0119410 A1 | 6/2003 | Bodaghi |
| 2003/0162460 A1 | 8/2003 | Saka et al. |
| 2003/0167044 A1 | 9/2003 | Toyoshima et al. |
| 2003/0181882 A1 | 9/2003 | Toyoshima et al. |
| 2003/0203162 A1 | 10/2003 | Fenwick et al. |
| 2003/0211802 A1 | 11/2003 | Keck et al. |
| 2004/0020579 A1 | 2/2004 | Durrance et al. |
| 2004/0058607 A1 | 3/2004 | Bodaghi |
| 2004/0087924 A1 | 5/2004 | Sroda et al. |
| 2004/0102124 A1 | 5/2004 | Suzuki |
| 2004/0175556 A1 | 9/2004 | Clark et al. |
| 2004/0206442 A1 * | 10/2004 | Sommer ............... D04H 1/4374 156/62.4 |
| 2005/0118389 A1 | 6/2005 | Wildeman |
| 2005/0136213 A1 | 6/2005 | Seth et al. |
| 2005/0244619 A1 | 11/2005 | Kauschke et al. |
| 2005/0261649 A1 | 11/2005 | Cohen |
| 2005/0261653 A1 | 11/2005 | Digiacomantonio et al. |
| 2005/0281976 A1 | 12/2005 | Curro et al. |
| 2006/0058772 A1 | 3/2006 | Karami |
| 2006/0069380 A1 | 3/2006 | Chen et al. |
| 2006/0122572 A1 | 6/2006 | Suarez |
| 2006/0141217 A1 | 6/2006 | Ellis et al. |
| 2006/0241558 A1 | 10/2006 | Ramshak |
| 2007/0020440 A1 | 1/2007 | Wong et al. |
| 2007/0026753 A1 | 2/2007 | Neely et al. |
| 2007/0036943 A1 | 2/2007 | Hirose et al. |
| 2007/0128411 A1 | 6/2007 | Kawai et al. |
| 2007/0130713 A1 | 6/2007 | Chen et al. |
| 2007/0172628 A1 | 7/2007 | Seth et al. |
| 2007/0254545 A1 | 11/2007 | Martin |
| 2007/0255247 A1 | 11/2007 | Moberg-Alehammar et al. |
| 2008/0010795 A1 | 1/2008 | Mizutani et al. |
| 2008/0015531 A1 | 1/2008 | Hird et al. |
| 2008/0085399 A1 | 4/2008 | Noda et al. |
| 2008/0108962 A1 | 5/2008 | Furuta et al. |
| 2008/0132865 A1 | 6/2008 | Li et al. |
| 2008/0172018 A1 | 7/2008 | Chien |
| 2008/0256768 A1 | 10/2008 | Lampila et al. |
| 2008/0275415 A1 | 11/2008 | Wheeler et al. |
| 2008/0294138 A1 | 11/2008 | Andersson et al. |
| 2008/0300562 A1 | 12/2008 | Ahoniemi et al. |
| 2009/0005752 A1 | 1/2009 | Suzuki et al. |
| 2009/0030391 A1 | 1/2009 | Hammons et al. |
| 2009/0221979 A1 | 9/2009 | Huang et al. |
| 2009/0247977 A1 | 10/2009 | Takeuchi et al. |
| 2009/0264851 A1 | 10/2009 | Richlen et al. |
| 2010/0108554 A1 | 5/2010 | Melius et al. |
| 2010/0209664 A1 | 8/2010 | Sato et al. |
| 2010/0249740 A1 | 9/2010 | Miyamoto et al. |
| 2010/0274208 A1 | 10/2010 | Gabrielii et al. |
| 2010/0312211 A1 | 12/2010 | Bond et al. |
| 2011/0042011 A1 | 2/2011 | Sato et al. |
| 2011/0151196 A1 | 6/2011 | Schmidt et al. |
| 2011/0250816 A1 | 10/2011 | Fujiwara et al. |
| 2012/0059343 A1 | 3/2012 | Kume et al. |
| 2012/0111483 A1 | 5/2012 | Schneider et al. |
| 2012/0141742 A1 | 6/2012 | Yamaguchi et al. |
| 2012/0171408 A1 | 7/2012 | Turner et al. |
| 2012/0177886 A1 | 7/2012 | Kanya et al. |
| 2012/0179125 A1 | 7/2012 | Kanya et al. |
| 2012/0179126 A1 | 7/2012 | Kanya et al. |
| 2012/0189814 A1 | 7/2012 | Coslett et al. |
| 2012/0226250 A1 | 9/2012 | Sato et al. |
| 2012/0282436 A1 * | 11/2012 | Coe ..................... B31F 1/07 428/131 |
| 2012/0310197 A1 | 12/2012 | Thomas |
| 2012/0330260 A1 | 12/2012 | Bishop et al. |
| 2013/0034686 A1 | 2/2013 | Mitsuno |
| 2013/0178811 A1 | 7/2013 | Kikuchi et al. |
| 2013/0178815 A1 | 7/2013 | Ohashi et al. |
| 2013/0211358 A1 | 8/2013 | Kikkawa et al. |
| 2013/0304009 A1 | 11/2013 | Wang et al. |
| 2014/0005622 A1 | 1/2014 | Wirtz et al. |
| 2014/0021626 A1 | 1/2014 | Takano et al. |
| 2014/0121623 A1 | 5/2014 | Kirby et al. |
| 2014/0121625 A1 | 5/2014 | Kirby et al. |
| 2014/0121626 A1 * | 5/2014 | Finn ..................... B32B 3/30 604/384 |
| 2014/0154459 A1 | 6/2014 | Krautkramer et al. |
| 2014/0234575 A1 | 8/2014 | Mitsuno et al. |
| 2015/0038933 A1 | 2/2015 | Day et al. |
| 2015/0282997 A1 | 10/2015 | Arizti et al. |
| 2015/0282998 A1 | 10/2015 | Arizti et al. |
| 2016/0039109 A1 | 2/2016 | Cecchetto et al. |
| 2016/0074256 A1 * | 3/2016 | Strube ............... A61F 13/51121 428/171 |
| 2016/0136011 A1 | 5/2016 | Peri et al. |
| 2016/0213520 A1 * | 7/2016 | Li ..................... D04H 18/04 |
| 2017/0119596 A1 | 5/2017 | Bewick-Sonntag et al. |
| 2017/0203542 A1 | 7/2017 | Ramaratnam et al. |
| 2017/0258649 A1 | 9/2017 | Rosati et al. |

(56) References Cited

U.S. PATENT DOCUMENTS

| | | | |
|---|---|---|---|
| 2017/0259524 A1 | 9/2017 | Neton et al. | |
| 2017/0312148 A1 | 11/2017 | Dobrosielska-Oura et al. | |
| 2017/0319404 A1* | 11/2017 | Bewick-Sonntag | B29C 43/222 |
| 2018/0228669 A1* | 8/2018 | Schneider | A61F 13/15642 |
| 2020/0337910 A1* | 10/2020 | Xu | A61F 13/53 |

FOREIGN PATENT DOCUMENTS

| | | | |
|---|---|---|---|
| CN | 1156485 A | 8/1997 | |
| CN | 1299258 A | 6/2001 | |
| CN | 1348026 A | 5/2002 | |
| CN | 1672669 A | 9/2005 | |
| CN | 1735394 A | 2/2006 | |
| CN | 1937983 A | 3/2007 | |
| CN | 2923758 Y | 7/2007 | |
| CN | 101065528 A | 10/2007 | |
| CN | 101370973 A | 2/2009 | |
| CN | 101522974 A | 9/2009 | |
| CN | 102264970 A | 11/2011 | |
| CN | 104010806 A | 8/2014 | |
| CN | 105188630 A | 12/2015 | |
| CN | 105208988 A | 12/2015 | |
| CN | 204939744 U | 1/2016 | |
| CN | 106255485 A | 12/2016 | |
| CN | 107847355 A | 3/2018 | |
| DE | 19737219 A1 | 3/1999 | |
| EM | 000648472 S | 6/2009 | |
| EP | 0341993 A1 | 11/1989 | |
| EP | 0418954 A2 | 3/1991 | |
| EP | 0432882 A2 | 6/1991 | |
| EP | 0446432 B1 | 8/1996 | |
| EP | 0687169 B1 | 11/1999 | |
| EP | 1190690 A2 | 3/2002 | |
| EP | 1209271 A1 | 5/2002 | |
| EP | 0863734 B1 | 6/2002 | |
| EP | 1059908 B1 | 10/2004 | |
| EP | 1207829 B1 | 8/2006 | |
| EP | 2157223 A1 | 2/2010 | |
| EP | 1902168 B1 | 7/2010 | |
| EP | 1803429 B1 | 12/2011 | |
| EP | 2159043 B1 | 6/2012 | |
| EP | 2505173 A1 | 10/2012 | |
| GB | 1088376 A | 10/1967 | |
| GB | 1395402 A | 5/1975 | |
| JP | 08109564 A | 4/1996 | |
| JP | 2000023715 A | 1/2000 | |
| JP | 3181195 B2 | 7/2001 | |
| JP | 2002173863 A | 6/2002 | |
| JP | 2002287228 A2 | 10/2002 | |
| JP | 1172567 S | 5/2003 | |
| JP | 3408078 B2 | 5/2003 | |
| JP | 3453031 B2 | 10/2003 | |
| JP | 2004113489 A | 4/2004 | |
| JP | 2004121701 A | 4/2004 | |
| JP | 1220443 S | 10/2004 | |
| JP | 2005312547 A | 11/2005 | |
| JP | 2005334374 A | 12/2005 | |
| JP | 2007190315 A | 8/2007 | |
| JP | 3989476 B2 | 10/2007 | |
| JP | 3989477 B2 | 10/2007 | |
| JP | 2008148807 A | 7/2008 | |
| JP | 2008161302 A | 7/2008 | |
| JP | 2008161319 A | 7/2008 | |
| JP | 2009050621 A | 3/2009 | |
| JP | 4301999 B2 | 7/2009 | |
| JP | 2009153556 A | 7/2009 | |
| JP | 2010024573 A | 2/2010 | |
| JP | 2010115352 A | 5/2010 | |
| JP | 2010133071 A | 6/2010 | |
| JP | 4566109 B2 | 10/2010 | |
| JP | 4627014 B2 | 2/2011 | |
| JP | 2011110317 A | 6/2011 | |
| JP | 4889273 B2 | 3/2012 | |
| JP | 5074301 B2 | 11/2012 | |
| JP | 5086035 B2 | 11/2012 | |
| JP | 5087419 B2 | 12/2012 | |
| JP | 1479504 S | 9/2013 | |
| KR | 20100040729 A | 4/2010 | |
| KR | 20180060050 A | 6/2018 | |
| WO | 1990004066 A2 | 4/1990 | |
| WO | 1991011161 A1 | 8/1991 | |
| WO | 1998052458 A1 | 11/1998 | |
| WO | 1999055532 A1 | 11/1999 | |
| WO | 2001072251 A1 | 10/2001 | |
| WO | 04062528 A2 | 7/2004 | |
| WO | 2004059061 A1 | 7/2004 | |
| WO | 2005007952 A2 | 1/2005 | |
| WO | 2005007962 A1 | 1/2005 | |
| WO | 2005065606 A1 | 7/2005 | |
| WO | 2006007307 A1 | 1/2006 | |
| WO | 2006007340 A1 | 1/2006 | |
| WO | 2006011724 A1 | 2/2006 | |
| WO | 09101591 A1 | 8/2009 | |
| WO | 2010074205 A1 | 7/2010 | |
| WO | 2012024576 A1 | 2/2012 | |
| WO | 2013047890 A1 | 4/2013 | |
| WO | 2013099624 A1 | 7/2013 | |
| WO | 2014204016 A1 | 12/2014 | |
| WO | 2016073713 A1 | 5/2016 | |

OTHER PUBLICATIONS

Lemere, Mark, "Nonwoven Bonding Technologies", p. 7, Image, Inda.org, http://www.inda.org/BIO/cab2012_444_PPT.pdf.

Newbusi, "Application of non-woven fabrics on diapers and their technical development trends", Industry News, Apr. 18, 2019.

Huddersfield Textiles, "Nonwoven Manufacturing", www.tikp.co.uk/knowledge/technology/nonwovens/under-construction/?prinl=true, Jul. 10, 2019.

Co-Pending U.S. Appl. No. 16/597,282, filed Oct. 9, 2019, by Hammond et al. for "Absorb ent Article".

Co-Pending U.S. Appl. No. 16/497,626, filed Sep. 25, 2019, by Beitz et al. for "Incorporation of Apertured Area Into An Absorbent Article".

* cited by examiner

PROCESS FOR MAKING FLUID-ENTANGLED LAMINATE WEBS WITH HOLLOW PROJECTIONS AND APERTURES

BACKGROUND OF THE INVENTION

Fibrous nonwoven web materials are in wide use in a number of applications including but not limited to absorbent structures and wiping products, many of which are disposable. In particular, such materials are commonly used in personal care absorbent articles such as diapers, diaper pants, training pants, feminine hygiene products, adult incontinence products, bandages and wiping products such as baby and adult wet wipes. In many of these applications, three-dimensionality and increased surface area are desirable attributes. This is particularly true with body contacting materials for the aforementioned personal care absorbent articles and cleaning products. One of the main functions of personal care absorbent articles is to absorb and retain body exudates such as blood, menses, urine and bowel movements. By providing fibrous nonwovens with hollow projections, several attributes can be achieved at the same time. First, by providing projections, the overall laminate can be made to have a higher degree of thickness while minimizing material used. Increased material thickness serves to enhance the separation of the skin of the user from the absorbent core, hence improving the prospect of drier skin. By providing projections, land areas are created between the projections that can temporarily distance exudates from the high points of the projections while the exudates are being absorbed, thus reducing skin contact and providing better skin benefits. Second, by providing such projections, the spread of exudates in the finished product may be reduced, hence exposing less skin to contamination. Third, by providing projections, the hollows can, themselves, serve as fluid reservoirs to temporarily store body exudates and then later allow the exudates to move vertically into subjacent layers of the overall product. Fourth, by reducing overall skin contact, the fibrous nonwoven laminate with such projections can provide a softer feel to the contacted skin thereby enhancing the tactile aesthetics of the layer and the overall product. Fifth, when such materials are used as body contacting liner materials for disposable absorbent articles, the liner material also serves the function of acting as a cleaning aid when the product is removed. This is especially the case with menses and lower viscosity bowel movements as are commonly encountered in conjunction with such products.

Other attempts have been made to provide fibrous nonwoven webs which will provide the above-mentioned attributes and fulfill the above-mentions tasks. One such approach has been the use of various types of embossing to create three-dimensionality. This works to an extent, however high basis weights are required to create a structure with significant topography. Furthermore, it is inherent in the embossing process that starting thickness is lost due to the fact that embossing is, by its nature, a crushing and bonding process. Furthermore, to "set" the embossments in a nonwoven fabric, the densified sections are typically fused to create weld points that are typically impervious to fluid. Hence, a part of the area for fluid to transit through the material is lost. Also, "setting" the fabric can cause the material to stiffen and become less soft to the touch.

Another approach to provide the above-mentioned attributes has been to form fibrous webs on three dimensional forming surfaces. The resulting structures typically have little resilience at low basis weights (assuming soft fibers with desirable aesthetic attributes are used) and the topography is significantly degraded when wound on a roll and put through subsequent converting processes. This is partly addressed in the three dimensional forming process by allowing the three dimensional shape to fill with fiber. However, this typically comes at a higher cost due to the usage of more material and at the cost of softness, as well as the fact that the resultant material becomes aesthetically unappealing for certain applications.

Another approach to provide the above-mentioned attributes has been to aperture a fibrous web. Depending on the process, this can generate a flat two dimensional web or a web with some three dimensionality where the displaced fiber is pushed out of the plane of the original web. Typically, the extent of the three-dimensionality is limited, and under sufficient load, the displaced fiber may be pushed back toward its original position resulting in at least partial closure of the aperture. Aperturing processes that attempt to "set" the displaced fiber outside the plane of the original web are also prone to degrading the softness of the starting web. Another obstacle is that apertured materials are typically incorporated into end products with the use of adhesives; but, due to the open structure of the apertures, adhesives will often readily penetrate through the apertures in the nonwoven from its underside to its top, exposed surface. This creates unwanted issues such as adhesive build-up in the converting process or creating unintended bonds between layers within the finished product. However, if the apertures can be incorporated into a nonwoven web in such a way to maintain their function and to not interfere with the function of other components, the apertures can contribute to the function of a skin-facing nonwoven web in an absorbent article. For example, the apertures can contribute to separating skin from exudates, reducing the spread of exudates and providing a pathway for exudates to pass through the skin-contacting nonwoven layer to other layers of the absorbent article. Each of these functional benefits contribute to keeping the skin of the wearer of the absorbent article cleaner.

Given the benefits of fibrous nonwoven materials having hollow projections described above, there remains an opportunity to provide an improved process for forming a fibrous nonwoven material having hollow projections that also includes apertures. Further, there remains an opportunity to provide a process for forming a fibrous nonwoven material having a pattern of apertures that is registered with a pattern of hollow projections.

SUMMARY OF THE INVENTION

The present invention is directed to the process and apparatus for making fluid-entangled laminates having a fibrous nonwoven layer with hollow projections and apertures.

In one aspect, the present invention is a process that includes the process steps of providing a projection forming surface defining a plurality of forming holes therein with the forming holes being spaced apart from one another and having land areas therebetween. The projection forming surface further defines a plurality of protrusions; the protrusions have an adjacent land area. The projection forming surface is capable of movement in a machine direction at a projection forming surface speed. A projection fluid entangling device is also provided which has a plurality of projection fluid jets capable of emitting a plurality of pressurized projection fluid streams of entangling fluid from the projection fluid jets in a direction towards the projection forming surface.

The next step of the process is providing a support layer having a first surface and an opposed second surface. The following step is providing a nonwoven projection web having a plurality of fibers and an opposed inner surface and an outer surface. The projection web is fed onto the projection forming surface with the outer surface of the projection web positioned adjacent to the projection forming surface. The opposed second surface of the support layer is fed onto the inner surface of the projection web. The next step of the process is directing a plurality of pressurized projection fluid streams of the entangling fluid from the plurality of projection fluid jets are directed in a direction from the first surface of the support layer towards the projection forming surface to cause the following to happen: a) a first plurality of the fibers in the projection web in a vicinity of the forming holes in the projection forming surface to be directed into the forming holes to form a plurality of projections extending outwardly from the outer surface of the projection web; b) formation of apertures through the support layer and the projection web at contact points with the protrusions; and c) a second plurality of the fibers in the projection web to become entangled with the support layer to form a laminate web. This entanglement may be the result of the fibers of the projection web entangling with the support layer or, when the support layer is a fibrous structure too, fibers of the support layer entangling with the fibers of the projection web or a combination of the two described entanglement processes. In addition, the first and second plurality of fibers in the projection web may be the same plurality of fibers, especially when the projections are closely spaced as the same fibers, if of sufficient length, can both form the projections and entangle with the support layer.

Following the formation of the projections in the projection web, the formation of apertures through the support layer and the projection web and the attachment of the projection web with the support layer to form the laminate web, the laminate web is removed from the projection forming surface. In certain executions of the process and apparatus, it is desirable that the direction of the plurality of fluid streams causes the formation of projections which are hollow.

In an additional aspect of this process of the invention, fibers of the projection web become entangled with fibers of the support layer along the circumferences (or perimeters) of the apertures. The protrusions on the projection forming surface that are used to form the apertures may have a contact shape that may be selected from pointed, dome-shaped or flat. The process of the invention may include the additional step of providing a secondary forming surface located between two of the projection fluid jets between the step of directing said plurality of pressurized projection fluid streams and the step of removing the laminate web. When this step is added, the laminate web passes between the projection forming surface and the secondary forming surface. With this execution, the secondary forming surface includes a plurality of receiving holes positioned to engage with the protrusions of the projection forming surface. The secondary forming surface assists with good formation of the apertures. In another aspect, good formation of the apertures may be achieved by having at least one of the projection fluid jets positioned in relation to the projection forming surface in such a way to focus the entangling fluid against the protrusions of the projection forming surface.

In a preferred design, the projection forming surface comprises a texturizing drum, though it is also possible to form the forming surface from a belt system or belt and wire system. In certain executions, it is desirable that the land areas of the projection forming surface not be fluid permeable, in other situations they can be permeable, especially when the forming surface is a porous forming wire. If desired, the forming surface can be formed with raised areas in addition to the holes so as to form depressions in the land areas of the fluid-entangled laminate web according to the present invention.

In alternate executions of the equipment, the projection web and/or the support layer can be fed into the projection forming process at the same speed as the projection forming surface is moving or at a faster or slower rate. In certain executions of the process, it is desirable that the projection web be fed onto the projection forming surface at a speed which is greater than a speed the support layer is fed onto the projection web. In other situations, it may be desirable to feed both the projection web and the support layer onto the projection forming surface at a speed which is greater than the speed of the projection forming surface. It has been found that overfeeding material into the process provides additional fibrous structure within the projection web for formation of the projections. The rate at which the material is fed into the process is called the overfeed ratio. It has been found that particularly well-formed projections can be made when the overfeed ratio is between about 10 and about 50 percent, meaning that the speed at which the material is fed into the process and apparatus is between about 10 percent and about 50 percent faster than the speed of the projection forming surface. This is particularly advantageous with respect to the overfeeding of the projection web into the process and apparatus.

In an alternate form of the process and equipment, a pre-lamination step is provided in advance of the projection forming step. In this embodiment, the equipment and process are provided with a lamination forming surface which is permeable to fluids. The lamination forming surface is capable of movement in a machine direction at a lamination forming speed. As with the other embodiment of the process and equipment, a projection forming surface is provided which defines a plurality of forming holes therein with the forming holes being spaced apart from one another and having land areas therebetween. The projection forming surface further defines a plurality of protrusions where the protrusions have an adjacent land area. The projection forming surface is also capable of movement in the machine direction at a projection forming surface speed. The equipment and process also include a lamination fluid entangling device having a plurality of lamination fluid jets capable of emitting a plurality of pressurized lamination fluid streams of entangling fluid from the lamination fluid jets in a direction towards the lamination forming surface and a projection fluid entangling device having a plurality of projection fluid jets capable of emitting a plurality of pressurized projection fluid streams of an entangling fluid from the projection fluid jets in a direction towards the projection forming surface.

As with the other process and equipment, the process includes a step of providing a support layer having an opposed first surface and a second surface. The process also includes a step of providing a projection web having a plurality of fibers and an opposed inner surface and an outer surface. The support layer and the projection web are fed onto the lamination forming surface at which point a plurality of pressurized lamination fluid streams of entangling fluid are directed from the plurality of lamination fluid jets into the support layer and the projection web to cause at least a portion of the fibers from the projection web to become entangled with the support layer to form a laminate web.

After the laminate web is formed, it is fed onto the projection forming surface with the outer surface of the projection web being adjacent the projection forming surface. Next, a plurality of pressurized projection fluid streams of the entangling fluid from the plurality of projection fluid jets are directed into the laminate web in a direction from the first surface of the support layer towards the projection forming surface to cause a first plurality of the fibers in the projection web in a vicinity of the forming holes in the projection forming surface to be directed into the forming holes to form a plurality of projections extending outwardly from the outer surface of the projection web. The plurality of pressurized projection fluid streams of the entangling fluid from the plurality of projection fluid jets are also directed into the laminate web to cause the formation of apertures through the laminate web at the contact points with the protrusions. The thus-formed fluid-entangled laminate web is then removed from the projection forming surface. In certain executions of the process and apparatus, it is desirable that the direction of the plurality of fluid streams causes the formation of projections which are hollow.

In the process which employs a lamination step prior to the projection forming step, the lamination may take place with either the support layer being the layer which is in direct contact with the lamination forming surface or with the projection web being in direct contact with the lamination forming surface. When the support layer is fed onto the lamination forming surface, its first surface will be adjacent the lamination forming surface and so the inner surface of the projection web is thus fed onto the second surface of the support layer. As a result, the plurality of pressurized lamination fluid streams of entangling fluid emanating from the pressurized lamination fluid jets are directed from the outer surface of the projection web towards the lamination forming surface to cause at least a portion of the fibers from the projection web to become entangled with the support layer to form the laminate web.

As with the first process, fibers of the projection web become entangled with fibers of the support layer along the circumferences (or perimeters) of the apertures. The protrusions on the projection forming surface that are used to form the apertures may have a contact shape that may be selected from pointed, dome-shaped or flat. The process of the invention may include the additional step of providing a secondary forming surface located between two of the projection fluid jets between the second step of directing said plurality of pressurized projection fluid streams and the step of removing the laminate web. When this step is added, the laminate web passes between the projection forming surface and the secondary forming surface. With this execution, the secondary forming surface includes a plurality of receiving holes positioned to engage with the protrusions of the projection forming surface. The process including the pre-lamination step may also have at least one of the projection fluid jets positioned in relation to the projection forming surface in such a way to focus the entangling fluid against the protrusions of the projection forming surface.

As with the first process, the projection forming surface may comprise a texturizing drum and in certain applications it is desirable that the land areas of the projection forming surface not be fluid permeable relative to the entangling fluid being used. It is also desirable that the plurality of pressurized projection fluid streams cause the formation of projections which are hollow. In addition, the projection web can be fed onto the support layer at a speed that is greater than the speed the support layer is fed onto the lamination forming surface. Alternatively, both the projection web and the support layer can be fed onto the lamination forming surface at a speed that is greater than the lamination forming surface speed. The overfeed ratio for the material being fed into the lamination forming portion of the process can be between about 10 and about 50 percent. Once the laminate web has been formed, it can be fed onto the projection forming surface at a speed that is greater than the projection forming surface speed.

These and other embodiments of the present invention are set forth in further detail below.

BRIEF DESCRIPTION OF THE DRAWINGS

A full and enabling disclosure of the present invention, including the best mode thereof is set forth more particularly in the remainder of the specification, which includes reference to the accompanying figures, in which.

Figure 1:
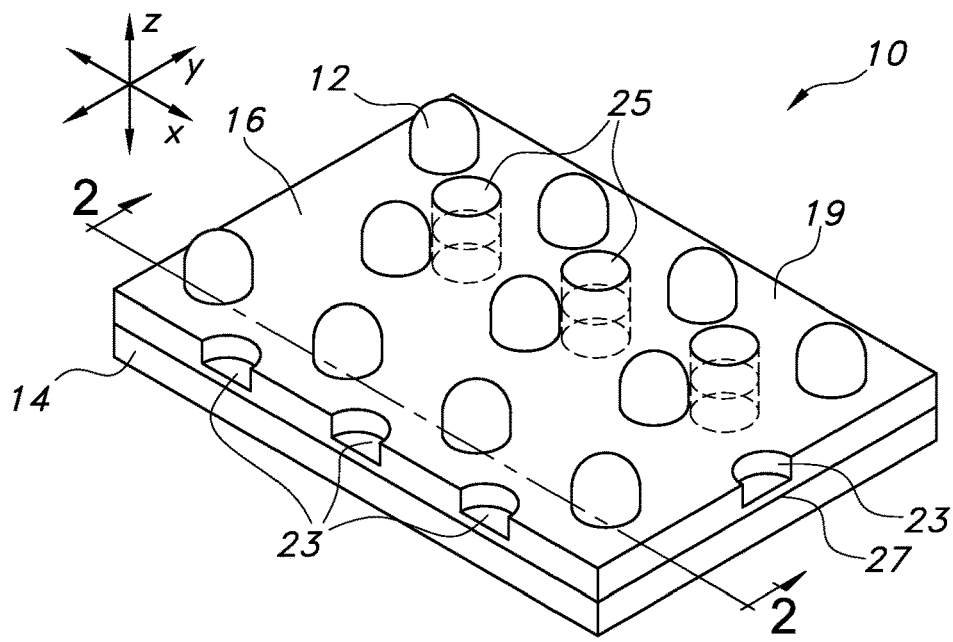
FIG. 1 is a perspective view of one embodiment of a fluid entangled laminate web according to the present invention.

Repeat use of reference characters in the present specification and drawings is intended to represent the same or analogous features or elements of the present invention.

DETAILED DESCRIPTION OF REPRESENTATIVE EMBODIMENTS

Definitions

As used herein the term "nonwoven fabric or web" refers to a web having a structure of individual fibers, filaments or threads (collectively referred to as "fibers" for sake of simplicity) which are interlaid, but not in an identifiable manner as in a knitted fabric. Nonwoven fabrics or webs have been formed from many processes such as for example, meltblowing processes, spunbonding processes, carded web processes, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns. To provide additional web integrity the webs so formed can be subjected to additional fiber bonding techniques if so desired. See for example, U.S. Pat. No. 3,855,046 to Hansen et al., which is incorporated herein in its entirety by reference thereto for all purposes.

As used herein, the term "carded web" generally refers to a web containing natural or synthetic staple length fibers typically having fiber lengths less than 100 millimeters. Bales of staple fibers undergo an opening process to separate the fibers which are then sent to a carding process which separates and combs the fibers to align them in the machine direction after which the fibers are deposited onto a moving wire for further processing. Such webs usually are subjected to some type of bonding process such as thermal bonding using heat and/or pressure. In addition or in lieu thereof, the fibers may be subject to adhesive processes to bind the fibers together such as by the use of powder adhesives. Still further, the carded web may be subjected to fluid entangling such as hydroentangling to further intertwine the fibers and thereby improve the integrity of the carded web. Carded webs due to the fiber alignment in the machine direction, once bonded, will typically have more machine direction strength than cross machine direction strength.

As used herein, the term "fluid entangling" and "fluid-entangled" generally refers to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) is then directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, their fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

Detailed Description of the Invention

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. When ranges for parameters are given, it is intended that each of the endpoints of the range are also included within the given range. It is to be understood by one of ordinary skill in the art that the present discussion is a description of exemplary embodiments only, and is not intended as limiting the broader aspects of the present invention, which broader aspects are embodied exemplary constructions.

Figure 2:
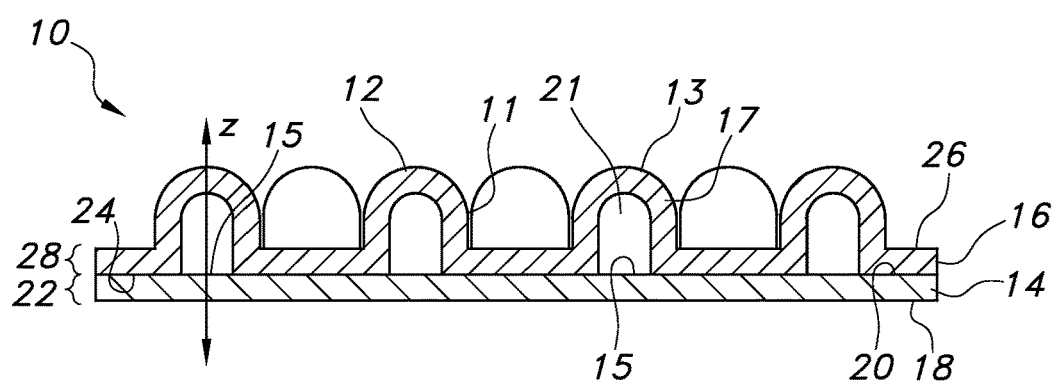
FIG. 2 is a cross-section of the material shown in FIG. 1 taken along line 2-2 of FIG. 1.
Figure 2A:
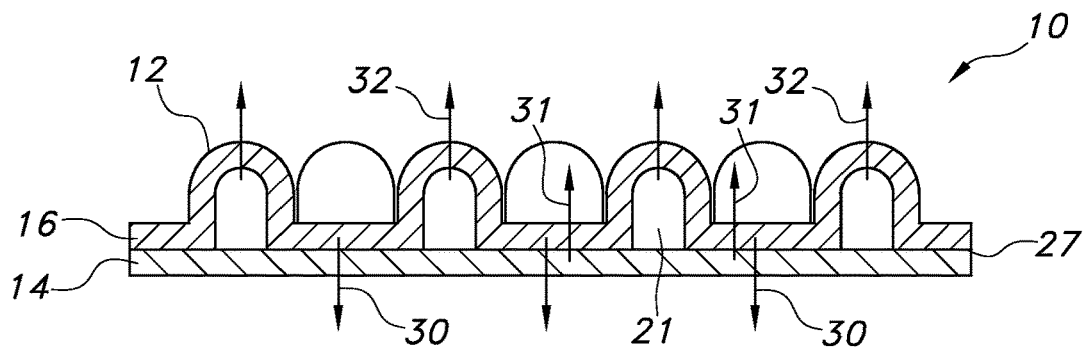
FIG. 2A is a cross-sectional view of the material according to the present invention taken along line 2-2 of FIG. 1 showing possible directions of fiber movements within the laminate due to the fluid-entanglement process according to the present invention.

The result of the processes and apparatus described herein is the generation of a fluid-entangled laminate web having projections extending outwardly and away from a surface of the laminate and having apertures interspersed with the projections. In preferred embodiments the projections are hollow. An embodiment of the present invention is shown in FIGS. 1, 2 and 2A of the drawings. A fluid-entangled laminate web 10 is shown with projections 12 which for many applications are desirably hollow. The web 10 includes a support layer 14 (which in FIGS. 1, 2 and 2A is shown as a fibrous nonwoven support web 14) and a fibrous nonwoven projection web 16. The support layer 14 has a first surface 18 and an opposed second surface 20 as well as a thickness 22. The projection web 16 has an inner surface 24 and an opposed outer surface 26 as well as a thickness 28. The interface between the support layer 14 and the projection web 16 is shown by reference number 27 and it is desirable that the fibers of the projection web 16 cross the interface 27 and be entangled with and engage the support layer 14 so as to form the laminate 10. When the support layer or web 14 is a fibrous nonwoven too, the fibers of this layer may cross the interface 27 and be entangled with the fibers in the projection web 16. The overall laminate 10 is referred to as a fluid-entangled laminate web due to the fibrous nature of the projection web 16 portion of the laminate 10 while it is understood that the support layer 14 is referred to as a layer as it may comprise fibrous web material such as nonwoven material but it also may comprise or include other materials such as, for example, films, scrims and foams. Generally for the end-use applications outlined herein, basis weights for the fluid-entangled laminate web 10 will range between about 25 and about 100 gsm though basis weights outside this range may be used depending upon the particular end-use application.

Hollow Projections

While the projections 12 can be filled with fibers from the projection web 16 and/or the support layer 14, it is generally desirable for the projections 12 to be generally hollow, especially when such laminates 10 are being used in connection with absorbent structures. The hollow projections 12 desirably have closed ends 13 which are devoid of holes or apertures. Such holes or apertures are to be distinguished from the normal interstitial fiber-to-fiber spacing commonly found in fibrous nonwoven webs. In some applications, however, it may be desirable to increase the pressure and/or dwell time of the impinging fluid jets in the entangling process as described below to create one or more holes or apertures (not shown) in one or more of the hollow projections 12. Such apertures may be formed in the ends 13 or side walls 11 of the projections 12 as well as in both the ends 13 and side walls 11 of the projections 12.

The hollow projections 12 shown in the Figures are round when viewed from above with somewhat domed or curved tops or ends 13 as seen when viewed in the cross-section. The actual shape of the projections 12 can be varied depending on the shape of the forming surface into which the fibers from the projection web 16 are forced. Thus, while not limiting the variations, the shapes of the projections 12 may be, for example, round, oval, square, rectangular, triangular, diamond-shaped, etc. Both the width and depth of the hollow projections 12 can be varied as can be the spacing and pattern of the projections 12. Further, various shapes, sizes and spacing of the projections 12 can be utilized in the same projection web 16.

The projections 12 in the laminate web 10 are located on and emanate from the outer surface 26 of the projection web 16. When the projections 12 are hollow, they will have open ends 15 which are located towards the inner surface 24 of the projection web 16 and are covered by the second surface 20 of the support layer or web 14 or the inner surface 24 of the projection web 16 depending upon the amount of fiber that has been used from the projection web 16 to form the projections 12. The projections 12 are surrounded by land areas 19 which are also formed from the outer surface 26 of the projection web 16 though the thickness of the land areas 19 is comprised of both the projection web 16 and the support layer 14. This land area 19 may be relatively flat and planar as shown in FIG. 1 or it may have topographical variability built into it. For example, the land area 19 may have a plurality of three-dimensional shapes formed into it by forming the projection web 16 on a three-dimensionally-shaped forming surface such as is disclosed in U.S. Pat. No. 4,741,941 to Englebert et al. assigned to Kimberly-Clark Worldwide and incorporated herein by reference in its entirety for all purposes. For example, the land areas 19 may be provided with depressions 23 which extend all or part way into the projection web 16 and/or the support layer 14. In addition, the land areas 19 may be subjected to embossing which can impart surface texture and other functional attributes to the land area 19. Still further, the land areas 19 and the laminate 10 as a whole may be provided with apertures 25 that are interspersed with the projections 12. The apertures 25 extend through the laminate 10 so as to further facilitate the movement of fluids (such as the liquids and solids that make up body exudates) into and through the laminate 10.

While it is possible to vary the density and fiber content of the projections 12, it is generally desirable that the projections 12 be "hollow". Referring to FIGS. 2 and 2A, it can be seen that when the projections 12 are hollow, they tend to form a shell 17 from the fibers of the projection web 16. The shell 17 defines an interior hollow space 21 which has a lower density of fibers as compared to the density of the shell 17 of the projections 12. By "density" it is meant the fiber count or content per chosen unit of volume within a portion of the interior hollow space 21 or the shell 17 of the projection 12. The thickness of the shell 17 as well as its density may vary within a particular or individual projection 12 and it also may vary as between different projections 12. In addition, the size of the hollow interior space 21 as well as its density may vary within a particular or individual projection 12 and it also may vary as between different projections 12. In some situations, there may not be a well-defined demarcation between the shell 17 and the interior hollow space 21 but, if at least some portion of the interior hollow space 21 of the projection 12 has a lower density than some portion of the shell 17 of the same projection 12, then the projection 12 is regarded as being "hollow". Further if at least a portion of the projections 12 of a fluid-entangled laminate web 10 are hollow, the projection web 16 and the laminate 10 are regarded as being "hollow" or as having "hollow projections". Typically the portion of the projections 12 which are hollow will be greater than or equal to 50 percent of the projections 12 in a chosen area of the fluid-entangled laminate web 10, alternatively greater than or equal to 70 percent of the projections in a chosen area of the fluid-entangled laminate web 10 and alternatively greater than or equal to 90 percent of the projections 10 in a chosen area of the fluid entangled laminate web 10.

As will become more apparent in connection with the description of the processes set forth below, the fluid-entangled laminate web 10 is the result of the movement of the fibers in the projection web 16 in one and sometimes two or more directions. Referring to FIGS. 2A and 3A, if the projection forming surface 130 upon which the projection web 16 is placed is solid except for the forming holes or apertures 134 used to form the hollow projections 12, then the force of the fluid entangling streams hitting and rebounding off the solid surface area 136 of the projection forming surface 130 corresponding to the land areas 19 of the projection web 16 can cause a migration of fibers adjacent the inner surface 24 of the projection web 16 into the support layer 14 adjacent its second surface 20. This migration of fibers in the first direction is represented by the arrows 30 shown in FIG. 2A. In order to form the hollow projections 12 extending outwardly from the outer surface 26 of the projection web 16, there must be a migration of fibers in a second direction as shown by the arrows 32. It is this migration in the second direction which causes fibers from the projection web 16 to move out and away from the outer surface 26 to form the hollow projections 12.

When the support layer 14 is a fibrous nonwoven web, depending on the degree of web integrity and the strength and dwell time of the entangling fluid from the pressurized fluid jets, there also may be a movement of support web fibers into the projection web 16 as shown by arrows 31 in FIG. 2A. The net result of these fiber movements is the creation of a laminate 10 with good overall integrity and lamination of the layer and web (14 and 16) at their interface 27 thereby permitting further processing and handling of the laminate 10. As a result of the fluid entanglement processes described herein, it is generally not desirable that the fluid pressure used to form the projections 12 be of sufficient force so as to force fibers from the support layer 14 to be exposed on the outer surface 26 of the projection web 16.

Support Layer and Projection Web

As the name implies, the support layer 14 is meant to support the projection web 16 containing the projections 12. The support layer 14 can be made from a number of structures provided the support layer 14 is capable of supporting the projection web 16. The primary functions of the support layer 14 are to protect the projection web 16 during the formation of the projections 12, to be able to bond to or be entangled with the projection web 16 and to aid in the further processing of the projection web 16 and the resultant fluid-entangled laminate web 10. Suitable materials for the support layer 14 can include, but are not limited to, nonwoven fabrics or webs, scrim materials, netting materials, paper/cellulose/wood pulp-based products which can be considered a subset of nonwoven fabrics or webs as well as foam materials, films and combinations of the foregoing provided the material or materials chosen are capable of withstanding the fluid-entangling process. A particularly well-suited material for the support layer 14 is a fibrous nonwoven web made from a plurality of randomly deposited fibers which may be staple length fibers such as are used, for example, in carded webs, air laid webs, etc. or they may be more continuous fibers such as are found in, for example, meltblown or spunbond webs. Due to the functions the support layer 14 must perform, the support layer 14 should have a higher degree of integrity than the projection web 16. In this regard, the support layer 14 should be able to remain substantially intact when it is subjected to the fluid-entangling process discussed in greater detail below. The degree of integrity of the support layer 14 should be such that the material forming the support layer 14 resists being driven down into and filling the hollow projections 12 of the projection web 16. As a result, when the support layer 14 is a fibrous nonwoven web, it is desirable that it should have a higher degree of fiber-to-fiber bonding and/or fiber entanglement than the fibers in the projection web 16. While it is desirable to have fibers from the support layer 14 entangle with the fibers of the projection web 16 adjacent the interface 27 between the two layers, it is generally desired that the fibers of this support layer 14 not be integrated or entangled into the projection web 16 to such a degree that large portions of these fibers find their way inside the hollow projections 12.

A function of the support layer 14 is to facilitate further processing of the projection web 16. Typically the fibers used to form the projection web 16 are more expensive than those used to form the support layer 14. As a result, it is desirable to keep the basis weight of the projection web 16 low. In so doing, however, it becomes difficult to process the projection web 16 subsequent to its formation. By attaching the projection web 16 to an underlying support layer 14, further processing, winding and unwinding, storage and other activities can be done more effectively.

In order to resist this higher degree of fiber movement, as mentioned above, it is desirable that the support layer 14 have a higher degree of integrity than the projection web 16. This higher degree of integrity can be brought about in a number of ways. One is fiber-to-fiber bonding which can be achieved through thermal or ultrasonic bonding of the fibers to one another with or without the use of pressure as in through air bonding, point bonding, powder bonding, chemical bonding, adhesive bonding, embossing, calender bonding, etc. In addition, other materials may be added to the fibrous mix such as adhesives and/or bicomponent fibers. Pre-entanglement of the fibrous nonwoven support layer 14 may also be used such as, for example, by subjecting the web to hydroentangling, needle punching, etc. prior to this web 14 being joined to the projection web 16. Combinations of the foregoing are also possible. Still other materials such as foams, scrims and nettings may have enough initial integrity so as to not need further processing. The level of integrity can in many cases be visually observed due to, for example, the observation with the unaided eye of such techniques as point bonding which is commonly used with fibrous nonwoven webs such as spunbond webs and staple fiber-containing webs. Further magnification of the support layer 14 may also reveal the use of fluid-entangling or the use of thermal and/or adhesive bonding to join the fibers together. Depending on whether samples of the individual layers (14 and 16) are available, tensile testing in either or both of the machine and cross-machine directions may be undertaken to compare the integrity of the support layer 14 to the projection web 16. See for example ASTM test D5035-11 which is incorporated herein its entirety for all purposes.

The type, basis weight, strength and other properties of the support layer 14 can be chosen and varied depending upon the particular end use of the resultant laminate 10. When the laminate 10 is to be used as part of an absorbent article such as a personal care absorbent article, wipe, etc., it is generally desirable that the support layer 14 be a layer that is fluid pervious, has good wet and dry strength, is able to absorb fluids such as body exudates, possibly retain the fluids for a certain period of time and then release the fluids to one or more subjacent layers. In this regard, fibrous nonwovens such as spunbond webs, meltblown webs and carded webs such as airlaid webs, bonded carded webs and coform materials are particularly well-suited as support layers 14. Foam materials and scrim materials are also well-suited. In addition, the support layer 14 may be a multi-layered material due to the use of several layers or the use of multi-bank formation processes as are commonly used in making spunbond webs and meltblown webs as well as layered combinations of meltblown and spunbond webs.

In the formation of such support layers 14, both natural and synthetic materials may be used alone or in combination to fabricate the material. Generally for the end-use applications outlined herein, support layer 14 basis weights will range between about 5 and about 40 gsm though basis weights outside this range may be used depending upon the particular end-use application.

The type, basis weight and porosity of the support web 14 will affect the process conditions necessary to form the projections 12 in the projection web 16. Heavier basis weight materials will increase the entangling force of the entangling fluid streams needed to form the projections 12 in the projection web 16. However, heavier basis weight support layers 14 will also provide improved support for the projection web 16 as a major problem with the projection web 16 by itself is that it is too stretchy to maintain the shape of the projections 12 post the formation process. The projection web 16 by itself unduly elongates in the machine direction due to the mechanical forces exerted on it by subsequent winding and converting processes which diminish and distort the projections 12. Also, without the support layer 14, the projections 12 in the projection web 16 collapse due to the winding pressures and compressive weights the projection web 16 experiences in the winding process and subsequent conversion and do not recover to the extent they do with the support layer 14.

The support layer 14 may be subjected to further treatment and/or additives to alter or enhance its properties. For example, surfactants and other chemicals may be added both internally and externally to the components forming all or a portion of the support layer 14 to alter or enhance its properties. Compounds commonly referred to as hydrogels or superabsorbents which absorb many times their weight in liquids may be added to the support layer 14 in both particulate and fiber form.

The projection web 16 is made from a plurality of randomly deposited fibers which may be staple length fibers such as those that are used, for example, in carded webs, airlaid webs, coform webs, etc. or they may be more continuous fibers such as those that are found in, for example, meltblown or spunbond webs. The fibers in the projection web 16 desirably should have less fiber-to-fiber bonding and/or fiber entanglement and thus less integrity as compared to the integrity of the support layer 14, especially when the support layer 14 is a fibrous nonwoven web. The fibers in the projection web 16 may have no initial fiber-to-fiber bonding for purposes of allowing the formation of the hollow projections 12 as will be explained in further detail below in connection with the description of one or more of the embodiments of the process and apparatus for forming the fluid-entangled laminate web 10. Alternatively, when both the support layer 14 and the projection web 16 are both fibrous nonwoven webs, the projection web 16 will have less integrity than the support web 14 due to the projection web 16 having, for example, less fiber-to-fiber bonding, less adhesive or less pre-entanglement of the fibers forming the web 16.

The projection web 16 must have a sufficient amount of fiber movement capability to allow the below-described fluid entangling process to be able to move fibers of the projection web 16 out of the X-Y plane of the projection web 16 as shown in FIG. 1 and into the perpendicular or Z-direction (the direction of its thickness 28) of the web 16 so as to be able to form the hollow projections 12. If more continuous fiber structures are being used such as meltblown or spunbond webs, it is desirable to have little or no pre-bonding of the projection web 16 prior to the fluid entanglement process. Longer fibers such as are generated in meltblowing and spunbonding processes (which are often referred to as continuous fibers to differentiate them from staple length fibers) will typically require more force to displace the fibers in the Z-direction than will shorter, staple length fibers that typically have fiber lengths less than 100 millimeters (mm) and more typically fiber lengths in the 10 to 60 mm range. Conversely, staple fiber webs such as carded webs and airlaid webs can have some degree of pre-bonding or entanglement of the fibers due to their shorter length. Such shorter fibers require less fluid force from the fluid entangling streams to move them in the Z-direction to form the hollow projections 12. As a result, a balance must be met between fiber length, degree of pre-fiber bonding, fluid force, web speed and dwell time so as to be able to create the hollow projections 12 without, unless desired, forming apertures in the land areas 19, the hollow projections 12, or forcing too much material into the interior hollow space 21 of the projections 12 thereby making the projections 12 too rigid for some end-use applications.

Generally, the projection web 16 will have a basis weight ranging between about 10 and about 60 gsm for the uses outlined herein but basis weights outside this range may be used depending upon the particular end-use application. Spunbond webs will typically have basis weights of between about 15 and about 50 grams per square meter (gsm) when being used as the projection web 16. Fiber diameters will range between about 5 and about 20 microns. The fibers may be single component fibers formed from a single polymer composition or they may be bicomponent or multicomponent fibers wherein one portion of the fiber has a lower melting point than the other components so as to allow fiber-to-fiber bonding through the use of heat and/or pressure. Hollow fibers may also be used. The fibers may be formed from any polymer formulations typically used to form spunbond webs. Examples of such polymers include, but are not limited to, polypropylene (PP), polyester (PET), polyamide (PA), polyethylene (PE) and polylactic acid (PLA). The spunbond webs may be subjected to post-formation bonding and entangling techniques if necessary to improve the processability of the web prior to it being subjected to the projection forming process.

Meltblown webs will typically have basis weights of between about 20 and about 50 grams per square meter (gsm) when being used as the projection web 16. Fiber diameters will range between about 0.5 and about 5 microns. The fibers may be single component fibers formed from a single polymer composition or they may be bicomponent or multicomponent fibers wherein one portion of the fiber has a lower melting point than the other components so as to allow fiber-to-fiber bonding through the use of heat and/or pressure. The fibers may be formed from any polymer formulations typically used to form the aforementioned spunbond webs. Examples of such polymers include, but are not limited to, PP, PET, PA, PE and PLA.

Carded and airlaid webs use staple fibers that will typically range in length between about 10 and about 100 millimeters. Fiber denier will range between about 0.5 and about 6 denier depending upon the particular end use. Basis weights will range between about 20 and about 60 gsm. The staple fibers may be made from a wide variety of polymers including, but not limited to, PP, PET, PA, PLA, cotton, rayon flax, wool, hemp and regenerated cellulose such as, for example, viscose. Blends of fibers may be utilized too such as blends of bicomponent fibers and single component fibers as well as blends of solid fibers and hollow fibers. If bonding is desired, it may be accomplished in a number of ways including, for example, through-air bonding, calender bonding, point bonding, chemical bonding and adhesive bonding such as powder bonding. If needed, to further enhance the integrity and processability of such webs prior to the projection forming process, they may be subjected to pre-entanglement processes to increase fiber entanglement within the projection web 16 prior to the formation of the projections 12. Hydroentangling is particularly advantageous in this regard.

While the foregoing nonwoven web types and formation processes are suitable for use in conjunction with the projection web 16, it is anticipated that other webs and formation processes may also be used provided the webs are capable of forming the hollow projections 12.

Process Description

To form the materials according to the present invention, a fluid entangling process must be employed. Any number of fluids may be used to join the support layer 14 and projection web 16 together, including both liquids and gases. The most common technology used in this regard is referred to as spunlace or hydroentangling technology which uses pressurized water as the fluid for entanglement. The process of the present invention is directed to formation of a fluid-entangled laminate web that has hollow projections and also has apertures interspersed with the hollow projections. Formation of a fluid-entangled laminate web having hollow projections is described in U.S. Pat. No. 9,327,473 to Finn et al., the subject matter and description of which is incorporated herein by reference.

Figure 3:
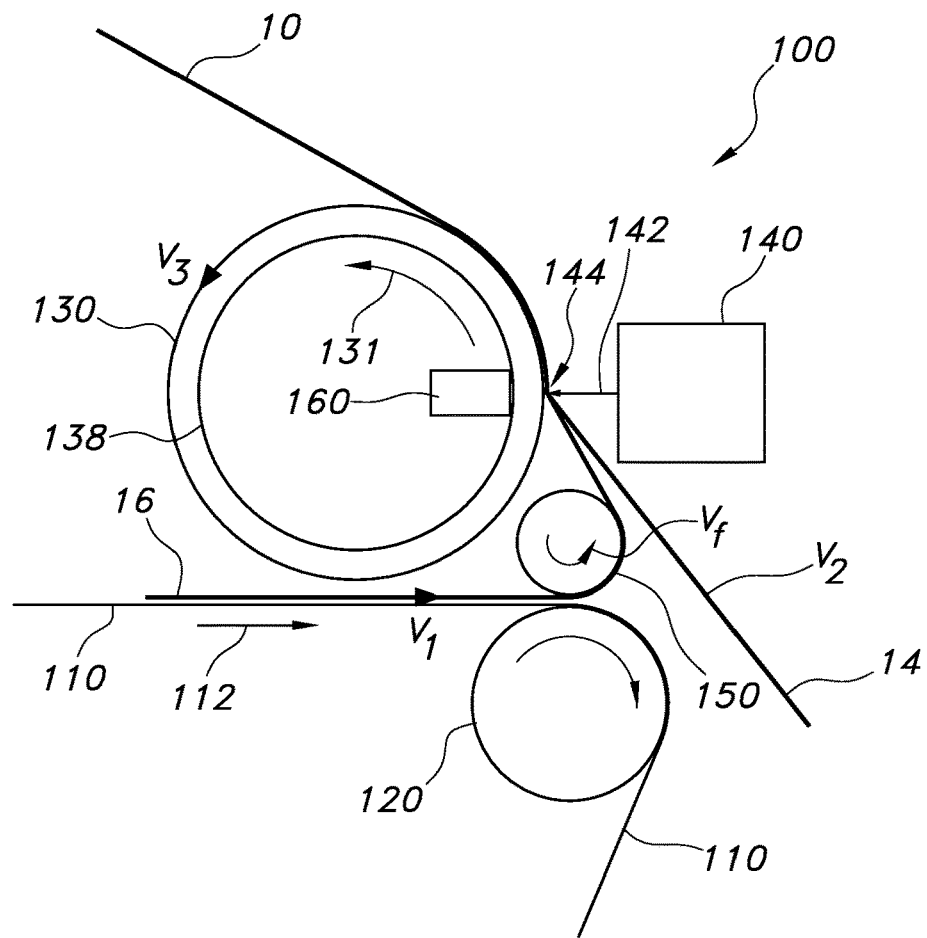
FIG. 3 is a schematic side view of an apparatus and process according to the present invention for forming a fluid-entangled laminate web according to the present invention.
Figure 3A:
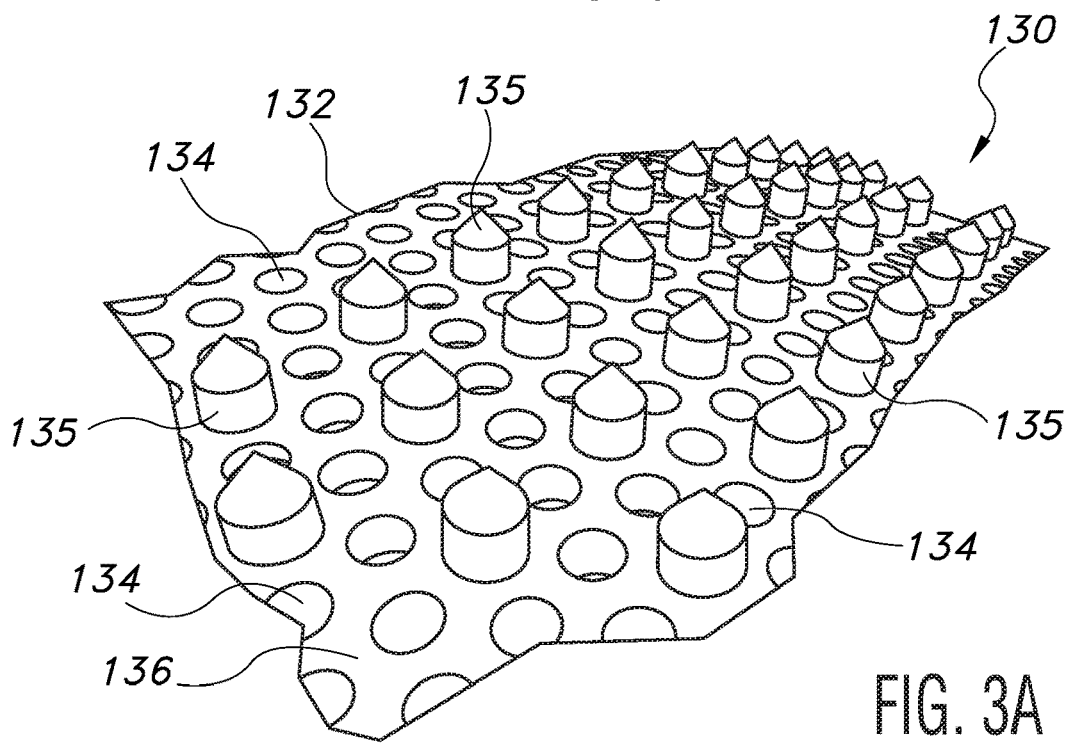
FIG. 3A is an exploded view of a representative portion of a projection forming surface according to the present invention.

Referring to FIG. 3 there is shown a first embodiment of a process and apparatus 100 for forming a fluid-entangled laminate web 10 with hollow projections 12 and apertures 25 according to the present invention. The apparatus 100 includes a first transport belt 110, a transport belt drive roll 120, a projection forming surface 130, a fluid entangling device 140, an optional overfeed roll 150, and a fluid removal system 160 such as a vacuum or other conventional suction device. Such vacuum devices and other means are well known to those of ordinary skill in the art. The transport belt 110 is used to carry the projection web 16 into the apparatus 100. If any pre-entangling is to be done on the projection web 16 upstream of the process shown in FIG. 3, the transport belt 110 may be porous. The transport belt 110 travels in a first direction (which is the machine direction) as shown by arrow 112 at a first speed or velocity V1. The transport belt 110 can be driven by the transport belt drive roller 120 or other suitable means as are well known to those of ordinary skill in the art.

The projection forming surface 130 as shown in FIG. 3 is in the form of a texturizing drum 130, a partially exploded view of the surface which is shown in FIG. 3A. The projection forming surface 130 moves in the machine direction as shown by arrow 131 in FIG. 3 at a speed or velocity V3. It is driven and its speed controlled by any suitable drive means (not shown) such as electric motors and gearing as are well known to those of ordinary skill in the art. The texturing drum 130 depicted in FIGS. 3 and 3A consists of a forming surface 132 containing a pattern of forming holes 134 that correspond to the shape and pattern of the desired projections 12 in the projection web 16. The forming holes 134 are separated by a land area 136. The forming holes 134 can be of any shape and any pattern. As can be seen from the Figures depicting the laminates 10 according to the present invention, the hole shapes are round but it should be understood that any number of shapes and combination of shapes can be used depending on the end use application. Examples of possible hole shapes include, but are not limited to, ovals, crosses, squares, rectangles, diamond shapes, hexagons and other polygons. Such shapes can be formed in the drum surface by casting, punching, stamping, laser-cutting and water-jet cutting. The spacing of the forming holes 134 and therefore the degree of land area 136 can also be varied depending upon the particular end application of the fluid-entangled laminate web 10. Further, the pattern of the forming holes 134 in the texturizing drum 130 can be varied depending upon the particular end application of the fluid-entangled laminate web 10. The material forming the texturizing drum 130 may be any number of suitable materials commonly used for such forming drums including, but not limited to, sheet metal, plastics and other polymer materials, rubber, etc. The forming holes 134 can be formed in a sheet of the material 132 that is then formed into a texturizing drum 130 or the texturizing drum 130 can be molded or cast from suitable materials or printed with 3D printing technology.

The forming surface 132 also contains a pattern of protrusions 135 that correspond to the shape and pattern of the desired apertures 25 in the laminate web 10. The protrusions 135 are adjacent land area 136. The protrusions 135 can be of any shape and any pattern. As can be seen from the Figures depicting the laminates 10 according to the present invention, the protrusions are "spike-shaped"/pointed to produce round apertures, but it should be understood that any number of shapes and combination of shapes can be used depending on the end use application of the laminate web. Examples of possible protrusion shapes include, but are not limited to, pointed, domed and flat; the protrusions can be further configured to produce apertures having any one of the following shapes: ovals, crosses, squares, rectangles, slots, knife edges, diamond shapes, hexagons and other polygons. The shape of the protrusion 135 may be varied, so long as the selected shape results in a protrusion 135 that is capable of moving the fibers of the support layer 14 and of the projection web 16 to form an aperture 25 in the laminate web 10 using the energy from the entangling fluid coming out of the projection fluid jets. The apertures 25 are formed at the contact points that the laminate web 10 has with the protrusions 135. As the protrusions 135 move the fibers of the laminate web 10 as it passes over the projection forming surface 130, the fibers of the laminate web 10 (fibers from the support layer 14 and the projection web 16) are pushed away from the opening of the aperture 25 and into the adjacent land area 19 and into the surrounding hollow projections 12. Fibers from the support layer 14 become entangled with fibers from the projection web 16 around the circumference/perimeter of the aperture 25. Therefore, placement of the protrusions 135 on the projection forming surface 130 does not cause the solid surface area 136 to go away. The solid surface area 136 provides a space for the fibers being pushed away from protrusions 135 that form apertures 25. The protrusions 135 can be formed in the drum surface by casting, weld attachment, machining, grinding, punching or stamping. Protrusions 135 can also be secured to projection forming surface 130 with screws, bolts, rivets, compression fittings, weld attachment, adhesive attachment, or other mechanical means. The spacing of the protrusions 135 and, therefore, the degree of land area 136 can also be varied depending upon the particular end application of the fluid-entangled laminate web 10. Further, the pattern of the protrusions 135 in the projection forming surface 130 can be varied depending upon the particular end application of the fluid-entangled laminate web 10. The protrusions 135 can be formed in a sheet of the material 132 that is then formed into the projection forming surface 130 or the projection forming surface 130 can be molded or cast from suitable materials or printed with 3D printing technology.

Typically, the perforated drum 130 is removably fitted onto and over an optional porous inner drum shell 138 so that different forming surfaces 132 can be used for different end product designs. The porous inner drum shell 138 interfaces with the fluid removal system 160 which facilitates pulling the entangling fluid and fibers down into the forming holes 134 in the outer texturizing drum surface 132 thereby forming the hollow projections 12 in the projection web 16. The porous inner drum shell 138 also acts as a barrier to retard further fiber movement down into the fluid removal system 160 and other portions of the equipment thereby reducing fouling of the equipment. The porous inner drum shell 138 rotates in the same direction and at the same speed as the texturizing drum 130. In addition, to further control the height of the projections 12, the distance between the inner drum shell 138 and the texturizing drum 130 can be varied. Generally, the spacing between the inner surface of projection forming surface 130 and the outer surface of the inner drum shell 138 will range between about 0 and about 5 mm. Other ranges can be used depending on the particular end-use application and the desired features of the fluid-entangled laminate web 10.

The depth of the forming holes 134 in the texturizing drum 130 or other projection forming surface 130 can be between 1 mm and 10 mm but preferably between around 3 mm and 5 mm to produce projections 12 with the shape most useful in the expected common applications. The hole cross-section size may be between about 2 mm and 10 mm but it is preferably between 3 mm and 6 mm as measured along the major axis and the spacing of the forming holes 134 on a center-to-center basis can be between 3 mm and 10 mm but preferably between 4 mm and 7 mm. The pattern of the spacing between forming holes 134 may be varied and selected depending upon the particular end use. Some examples of patterns include, but are not limited to, aligned patterns of rows and/or columns, skewed patterns, hexagonal patterns, wavy patterns and patterns depicting pictures, figures and objects.

The cross-sectional dimensions of the forming holes 134 and their depth influence the cross-section and height of the projections 12 produced in the projection web 16. Generally, hole shapes with sharp or narrow corners at the leading edge of the forming holes 134 as viewed in the machine direction 131 should be avoided as they can sometimes impair the ability to safely remove the fluid-entangled laminate web 10 from the forming surface 132 without damage to the projections 12. In addition, the thickness/hole depth in the texturizing drum 130 will generally tend to correspond to the depth or height of the hollow projections 12. It should be noted, however, that each of the hole depth, spacing, size, shape and other parameters may be varied independently of one another and may be varied based upon the particular end use of the fluid-entangled laminate web 10 being formed.

The land areas 136 in the forming surface 132 of the texturizing drum 130 are typically solid so as to not pass the entangling fluid 142 emanating from the pressurized fluid jets contained in the fluid entangling devices 140 but in some instances it may be desirable to make the land areas 136 fluid permeable to further texturize the exposed surface of the projection web 16. Alternatively, select areas of the forming surface 132 of the texturizing drum 130 may be fluid pervious and other areas impervious. For example, a central zone (not shown) of the texturizing drum 130 may be fluid pervious while lateral regions (not shown) on either side of the central region may be fluid impervious.

The land areas 136 in the forming surface 132 may be configured to form optional dimples 23 in the projection web 16 and the fluid-entangled laminate web 10. The height of the protrusions 135 in the texturizing drum 130 or other projection forming surface 130 can be between 1 mm and 10 mm but preferably between around 3 mm and 5 mm to produce apertures 25 that are fully-formed through the laminate web 10. The protrusion cross-section size may be between about 2 mm and 10 mm but it is preferably between 3 mm and 6 mm as measured along the major axis. The spacing between protrusions 135 on the forming surface 132 may be selected based on the location and/or pattern of apertures 25 desired in the laminate web 10. The spacing between protrusions 135 may be selected based on the desired registration with the forming holes 134. In one aspect, the spacing of the protrusions 135 on a center-to-center basis may be between 3 mm and 100 mm. In another aspect, the spacing of the protrusions 135 may be between 5 mm and 30 mm on a center-to-center basis. In a further aspect, the pattern of spacing between protrusions 135 may be non-uniform such that there is a higher density of protrusions 135 in one area/location of the forming surface 132 than in a neighboring area/location. The neighboring areas/locations on the forming surface 132 may be around the circumference of the forming surface 132 or across the width of the forming surface 132. In a representative aspect, the protrusions 135 are arranged in "array lanes"; an "array lane" is a pattern of protrusions 135 that may extend across the width of the forming surface 132. A group of array lanes may be located in proximity to each other to form a bigger pattern of protrusions 135; the array lanes may be separated from each other by a distance in the circumferential direction of the forming surface 132. An advantage of a non-uniform distribution of protrusions 135 on the forming surface 132 may be to provide areas without apertures 25 in the laminate web 10 to facilitate adhesive bonding of non-apertured areas of the laminate web 10 within an absorbent article to minimize risk of exposed adhesive.

In the embodiment of the apparatus 100 shown in FIG. 3, the projection forming surface 130 is shown in the form of a texturizing drum. It should be appreciated however that other means may be used to create the projection forming surface 130. For example, a foraminous belt or wire (not shown) may be used which includes forming holes 134 formed in the belt or wire at appropriate locations. Alternatively, flexible rubberized belts (not shown) which are impervious to the pressurized fluid entangling streams save the forming holes 134 may be used. Such belts and wires are well known to those of ordinary skill in the art as are the means for driving and controlling the speed of such belts and wires. A texturizing drum 130 is more advantageous for formation of the fluid-entangled laminate web 10 according to the present invention because it can be made with land areas 136 which are smooth and impervious to the entangling fluid 142 and which do not leave a wire weave pattern on the outer surface 26 of the projection web 16 as wire belts tend to do.

An alternative to a forming surface 132 with a hole-depth defining the projection height is a forming surface 132 that is thinner than the desired projection height but which is spaced away from the porous inner drum shell 138 surface on which it is wrapped. The spacing between the texturizing drum 130 and porous inner drum shell 138 may be achieved by any means that preferably does not otherwise interfere with the process of forming the hollow projections 12 and withdrawing the entangling fluid from the equipment. For example, one means is a hard wire or filament that may be inserted between the outer texturizing drum 130 and the porous inner drum shell 138 as a spacer or wrapped around the inner porous drum shell 138 underneath the texturizing drum 130 to provide the appropriate spacing. A shell depth of the forming surface 132 of less than 2 mm can make it more difficult to remove the projection web 16 and the laminate 10 from the texturizing drum 130 because the fibrous material of the projection web 16 can expand or be moved by entangling fluid flow into the overhanging area beneath the texturizing drum 130 which in turn can distort the resultant fluid-entangled laminate web 10. It has been found, however, that by using a support layer 14 in conjunction with the projection web 16 as part of the formation process, distortion of the resultant two layer fluid-entangled laminate web 10 can be greatly reduced. Use of the support web 14 generally facilitates cleaner removal of the fluid-entangled laminate web 10 because the less extensible, more dimensionally stable support layer 14 takes the load while the fluid-entangled laminate 10 is removed from the texturizing drum 130. The higher tension that can be applied to the support layer 14, compared to a single projection web 16, means that as the fluid-entangled laminate 10 moves away from the texturizing drum 130, the projections 12 can exit the forming holes 134 smoothly in a direction roughly perpendicular to the forming surface 132 and co-axially with the forming holes 134 in the texturizing drum 130. In addition, by using the support layer 14, processing speeds can be increased.

To form the projections 12 in the projection web 16, to laminate the support layer 14 and the projection web 16 together and to form apertures 25 in the laminate web 10, one or more fluid entangling devices 140 are spaced above the projection forming surface 130. The most common technology used in this regard is referred to as spunlace or hydroentangling technology which uses pressurize water as the fluid for entanglement. As an unbonded or relatively unbonded web or webs are fed into a fluid-entangling device 140, a multitude of high pressure fluid jets (not shown) from one or more fluid entangling devices 140 move the fibers of the webs and the fluid turbulence causes the fibers to entangle. These fluid streams, which in this case are water, can cause the fibers to be further entangled within the individual webs. The streams can also cause fiber movement and entanglement at the interface 27 of two or more webs/layers thereby causing the webs/layers to become joined together. Still further, if the fibers in a web, such as the projection web 16, are loosely held together, they can be driven out of their X-Y plane and thus in the Z-direction (see FIGS. 1 and 2A) to form the projections 12 which are preferably hollow. Depending on the level of entanglement needed, one or a plurality of such fluid entangling devices 140 can be used.

In FIG. 3 a single fluid entangling device 140 is shown but in succeeding Figures where multiple devices 140 are used in various regions of the apparatus 100, they are labeled with letter designators such as 140a, 140b, 140c, 140d and 140e. When multiple devices are used, the entangling fluid pressure in each subsequent fluid entangling device 140 is usually higher than the preceding one so that the energy imparted to the webs/layers increases and so the fiber entanglement within or between the webs/layers increases. This reduces disruption of the overall evenness of the areal density of the web/layer by the pressurized fluid jets while achieving the desired level of entanglement and hence bonding of the webs/layers and formation of the projections 12. The entangling fluid 142 of the fluid entangling devices 140 emanates from injectors via jet packs or strips (not shown) consisting of a row or rows of pressurized fluid jets with small apertures of a diameter usually between 0.08 and 0.15 mm and spacing of around 0.5 mm in the cross-machine direction. The pressure in the jets can be between about 5 bar and about 400 bar but typically is less than 200 bar except for heavy fluid-entangled laminate webs 10 and when fibrillation is required. Other jet sizes, spacings, numbers of jets and jet pressures can be used depending upon the particular end application. Such fluid entangling devices 140 are well known to those of ordinary skill in the art and are readily available from such manufactures as Fleissner of Germany and Andritz-Perfojet of France.

The fluid entangling devices 140 will typically have the jet orifices positioned or spaced between about 20 millimeters and about 40 millimeters, and more typically between about 20 and about 30 millimeters, from the projection forming surface 130 though the actual spacing can vary depending on the basis weights of the materials being acted upon, the fluid pressure, the number of individual jets being used, the amount of vacuum being used via the fluid removal system 160 and the speed at which the equipment is being run.

In the embodiments shown in FIGS. 3 through 7 the fluid entangling devices 140 are conventional hydroentangling devices the construction and operation of which are well known to those of ordinary skill in the art. See for example U.S. Pat. No. 3,485,706 to Evans, the contents of which is incorporated herein by reference in its entirety for all purposes. Also see the description of the hydraulic entanglement equipment described by Honeycomb Systems, Inc., Biddeford, Me., in the article entitled "Rotary Hydraulic Entanglement of Nonwovens", reprinted from INSIGHT '86 INTERNATIONAL ADVANCED FORMING/BONDING Conference, the contents of which is incorporated herein by reference in its entirety for all purposes.

Returning again to FIG. 3, the projection web 16 is fed into the apparatus and process 100 at a speed V1, the support layer 14 is fed into the apparatus and process 100 at a speed V2 and the fluid-entangled laminate web 10 exits the apparatus and process 100 at a speed V3 which is the speed of the projection forming surface 130 and can also be referred to as the projection forming surface speed. As will be explained in greater detail below, these speeds V1, V2, and V3 may be the same as one another or varied to change the formation process and the properties of the resultant fluid-entangled laminate web 10. Feeding both the projection web 16 and the support layer 14 into the process at the same speed (V1 and V2) will produce a fluid-entangled laminate web 10 according to the present invention with the desired hollow projections 12. Feeding both the projection web 16 and the support layer 14 into the process at the same speed which is faster than the machine direction speed (V3) of the projection forming surface 130 will also form the desired hollow projections 12.

Also shown in FIG. 3 is an optional overfeed roll 150 which may be driven at a speed or rate Vf. The overfeed roll 150 may be run at the same speed as the speed V1 of the projection web 16 in which case Vf will equal V1 or it may be run at a faster rate to tension the projection web 16 upstream of the overfeed roll 150 when overfeed is desired. Over-feed occurs when one or both of the incoming webs/layers (16, 14) are fed onto the projection forming surface 130 at a greater speed than the projection forming surface speed of the projection forming surface 130. It has been found that improved projection formation in the projection web 16 can be affected by feeding the projection web 16 onto the projection forming surface 130 at a higher rate than the incoming speed V2 of the support layer 14. In addition, however, it has been discovered that improved properties and projection formation can be accomplished by varying the feed rates of the webs/layers (16, 14) and by also using the overfeed roll 150 just upstream of the texturizing drum 130 to supply a greater amount of fiber via the projection web 16 for subsequent movement by the entangling fluid 142 down into the forming holes 134 in the texturizing drum 130. In particular, by overfeeding the projection web 16 onto the texturizing drum 130, improved projection formation can be achieved including increased projection height.

In order to provide an excess of fiber so that the height of the projections 12 is maximized, the projection web 16 can be fed onto the texturing drum 130 at a greater surface speed (V1) than the texturizing drum 130 is traveling (V3). Referring to FIG. 3, when overfeed is desired, the projection web 16 is fed onto the texturizing drum 130 at a speed V1 while the support layer 14 is fed in at a speed V2 and the texturizing drum 130 is traveling at a speed V3 which is slower than V1 and can be equal to V2. The overfeed percent or ratio, the ratio at which the projection web 16 is fed onto the texturizing drum 130, can be defined as $OF=[(V1/V3)-1] \times 100$ where V1 is the input speed of the projection web 16 and V3 is the output speed of the resultant fluid-entangled laminate web 10 and the speed of the texturizing drum 130. (When the overfeed roll 150 is being used to increase the speed of the incoming material onto the texturizing drum 130 it should be noted that the speed V1 of the material after the overfeed roll 150 will be faster than the speed V1 upstream of the overfeed roll 150. In calculating the overfeed ratio, it is this faster speed Vf that should be used.) Good formation of the projections 12 has been found to occur when the overfeed ratio is between about 10 and about 50 percent. Note too, that this overfeeding technique and ratio can be used with respect to not just the projection web 16 only but to a combination of the projection web 16 and the support layer 14 as they are collectively fed onto the projection forming surface 130.

In order to minimize the length of projection web 16 that is supporting its own weight before being subjected to the entangling fluid 142 and to avoid wrinkling and folding of the projection web 16, the overfeed roll 150 can be used to carry the projection web 16 at speed V1 to a position close to the texturizing zone 144 on the texturizing drum 130. In the example illustrated in FIG. 3, the overfeed roll 150 is driven off the transport belt 110 but it is also possible to drive it separately so as to not put undue stress on the incoming projection web material 16. The support layer 14 may be fed into the texturizing zone 144 separately from the projection web 16 and at a speed V2 that may be greater than, equal to or less than the texturizing drum speed V3 and greater than, equal to or less than the projection web 16 speed V1. Preferably the support layer 14 is drawn into the texturizing zone 144 by its frictional engagement with the projection web 16 positioned on the texturizing drum 130 and so once on the texturizing drum 130, the support layer 14 has a surface speed close to the speed V3 of the texturizing drum 130 or it may be positively fed into the texturizing zone 144 at a speed close to the texturizing drum speed of V3. The texturizing process causes some contraction of the support layer 14 in the machine direction 131. The overfeed of either the support layer 14 or the projection web 16 can be adjusted according to the particular materials and the equipment and conditions being used so that the excess material that is fed into the texturizing zone 144 is used up thereby avoiding any unsightly wrinkling in the resultant fluid-entangled laminate web 10. As a result, the two webs/layers (16, 14) will usually be under some tension at all times despite the overfeeding process. The take-off speed of the fluid-entangled laminate web 10 must be arranged to be to be close to the texturizing drum speed V3 such that excessive tension is not applied to the laminate in its removal from the texturizing drum 130 as such excessive tension would be detrimental to the clarity and size of the projections.

Figure 4:
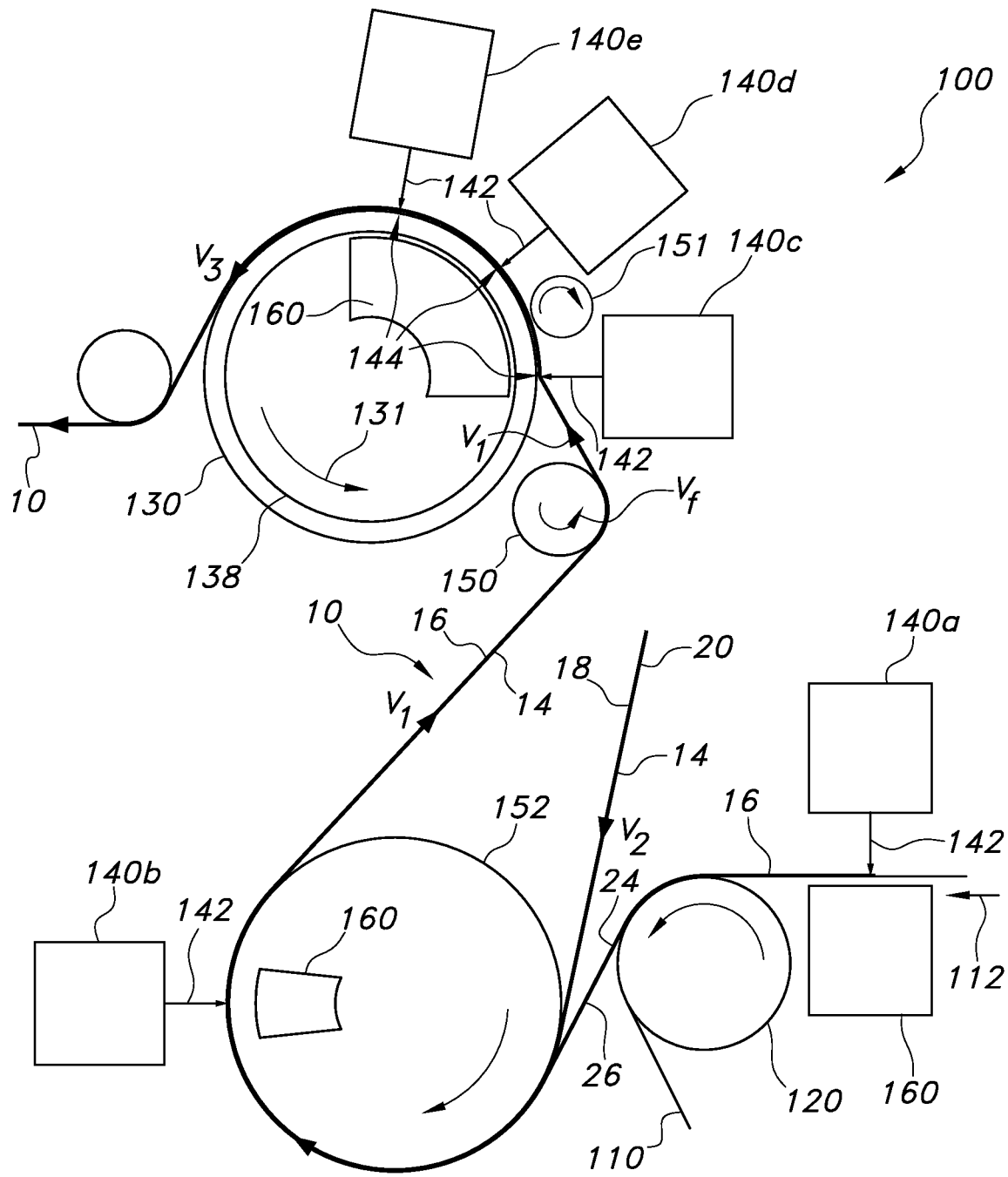
FIG. 4 is a schematic side view of an alternate apparatus and process according to the present invention for forming a fluid-entangled laminate web according to the present invention.

An alternate embodiment of the process and apparatus 100 according to the present invention is shown in FIG. 4 in which like reference numerals are used for like elements. In this embodiment the main differences are a pre-entanglement of the projection web 16 to improve its integrity prior to further processing via a pre-entanglement fluid entangling device 140a; a lamination of the projection web 16 to the support layer 14 via a lamination fluid entangling device 140b; and an increase in the number of fluid-entangling devices 140 (referred to as projection fluid entangling devices 140c, 140d and 140e) and thus an enlargement of the texturizing zone 144 on the texturizing drum 130 in the projection forming portion of the process.

The projection web 16 is supplied to the process/apparatus 100 via the transport belt 110. As the projection web 16 travels on the transfer belt 110 it is subjected to a first fluid entangling device 140a to improve the integrity of the projection web 16. This can be referred to as pre-entanglement of the projection web 16. As a result, this transport belt 110 should be fluid pervious to allow the entangling fluid 142 to pass through the projection web 16 and the transport belt 110. To remove the delivered entangling fluid 142, as in FIG. 3, a fluid removal system 160 such as a vacuum or other conventional fluid removal device may be used below the transport belt 110. The fluid pressure from the first fluid entangling device 140a is generally in the range of about 10 to about 50 bar.

The support layer 14 and the projection web 16 are then fed to a lamination forming surface 152 with the first surface 18 of the support web or layer 14 facing and contacting the lamination forming surface 152 and the second surface 20 of the support layer 14 contacting the inner surface 24 of the projection web 16. (See FIGS. 2 and 4.) To entangle the support layer 14 and the projection web 16 together, one or more lamination fluid entangling devices 140b are used in connection with the lamination forming surface 152 to affect fiber entanglement between the materials. Once again, a fluid removal system 160 is used to dispose of the entangling fluid 142. To distinguish the apparatus in this lamination portion of the overall apparatus and process 100 from the subsequent projection forming portion where the projections are formed, this equipment and process are referred to as lamination equipment as opposed to projection forming equipment. Thus, this portion is referred to as using a lamination forming surface 152 and a lamination fluid entangling device 140b which uses lamination fluid jets as opposed to projection forming jets. The lamination forming surface 152 is movable in the machine direction of the apparatus 100 at a lamination forming surface speed and should be permeable to the entangling fluid emanating from the lamination fluid jets located in the lamination fluid entangling device 140b. The lamination fluid entangling device 140b has a plurality of lamination fluid jets which are capable of emitting a plurality of pressurized lamination fluid streams of entangling fluid 142 in a direction towards the lamination forming surface 152. The lamination forming surface 152, when in the configuration of a drum as shown in FIG. 4, can have a plurality of forming holes in its surface separated by land areas to make it fluid permeable or it can be made from conventional forming wire which is permeable as well. In this portion of the apparatus 100, complete bonding of the two materials (14 and 16) is not necessary. Process parameters for this portion of the equipment are similar to those for the projection forming portion and the description of the equipment and process in connection with FIG. 3. Thus, the speeds of the materials and surfaces in the lamination forming portion of the equipment and process may be varied as explained above with respect to the projection forming equipment and process described with respect to FIG. 3.

For example, the projection web 16 may be fed into the lamination forming process and onto the support layer 14 at a speed that is greater than the speed the support layer 14 is fed onto the lamination forming surface 152. Relative to entangling fluid pressures, lower lamination fluid jet pressures are desired in this portion of the equipment as additional entanglement of the webs/layers will occur during the projection forming portion of the process. As a result, lamination forming pressures from the lamination entangling device 140b will usually range between about 30 and about 100 bar.

When the plurality of lamination fluid streams 142 in the lamination fluid entangling device 140b are directed in a direction from the outer surface 26 of the projection web 16 towards the lamination forming surface 152, at least a portion of the fibers in the projection web 16 are caused to become entangled with support layer 14 to form a laminate web 10. Once the projection web 16 and support layer 14 are joined into a laminate 10, the laminate 10 leaves the lamination portion of the equipment and process (elements 140b and 152) and is fed into the projection forming portion of the equipment and process (elements 130, 140c, 140d, 140e and optional 150). As with the process shown in FIG. 3, the laminate 10 may be fed onto the projection forming surface/ texturizing drum 130 at the same speed as the texturizing drum 130 is traveling or it may be overfed onto the texturizing drum 130 using the overfeed roll 150 or by simply causing the laminate 10 to travel at a speed V1 which is greater than the speed V3 of the projection forming surface 130. As a result, the process variables described above with respect to FIG. 3 of the drawings may also be employed with the equipment and process shown in FIG. 4. In addition, as with the apparatus and materials in FIG. 3, if the overfeed roll 150 is used to increase the speed V1 of the laminate 10 as it comes in contact with the projection forming surface 130, it is this faster speed V1 after the overfeed roll 150 that should be used when calculating the overfeed ratio. The same approach should be used when calculating the overfeed ratio with the remainder of the embodiments shown in FIGS. 4a, 5, 6 and 7 if overfeed of material is being employed.

In the projection forming portion of the equipment, a plurality of pressurized projection fluid streams of entangling fluid 142 are directed from the projection fluid jets located in the projection fluid entangling devices (140c, 140d and 140e) into the laminate web 10 in a direction from the first surface 18 of the support layer 14 towards the projection forming surface 130 to cause a first plurality of the fibers of the projection web 16 in the vicinity of the forming holes 134 located in the projection forming surface 130 to be directed into the forming holes 134 to form the plurality of projections 12 which extend outwardly from the outer surface 26 of the projection web 16 thereby forming the fluid-entangled laminate web 10 according to the present invention. The pressurized projection fluid streams of entangling fluid 142 also push the laminate web 10 against the projection forming surface 130 so that the fibers of the laminate web 10 are pushed over and around the protrusions 135 to form the plurality of apertures 25. As with the other processes, the formed laminate 10 is removed from the projection forming surface 130 and, if desired, may be subjected to the same or different further processing as described with respect to the process and apparatus in FIG. 3 such as drying to remove excess entangling fluid or further bonding or other steps. In the projection forming portion of the equipment and apparatus 100 projection, forming pressures from the projection fluid entangling devices (140c, 140d and 140e) will usually range between about 80 and about 200 bar.

In another aspect of the process and apparatus of the present invention, a step of providing one or more secondary forming surfaces may be added. For example, as shown in FIG. 4, one or more secondary forming surfaces 151 (similar in configuration to optional overfeed roll 150) may be located between two of the projection fluid jets located in the projection fluid entangling devices (140c, 140d and 140e). More specifically, one or more secondary forming surfaces 151 may be located between any two of fluid entangling devices 140c, 140d and 140e. The laminate web 10 than passes between the projection forming surface 130 and the secondary forming surfaces 151. The secondary forming surfaces 151 may cause additional pressure (caused by contact with the secondary forming surfaces) against the first surface 18 of the support layer 14. The additional pressure provides additional force to push the fibers of the laminate web 10 over and around the protrusions 135 on the forming surface 130. To further achieve this purpose of enabling better formation of the apertures 25 in the finished laminate web 10, the secondary forming surfaces 151 may include a plurality of receiving holes that are positioned and configured to receive the protrusions 135 extending outward from the projection forming surface 130. The shapes and dimensions of such receiving holes are selected to provide for sufficient void space to receive the corresponding protrusions 135 from the forming surface 130 plus the space needed to accommodate the laminate web 10 while providing the intended magnitude of pressure on the laminate web 10 as it passes through the interlocking combination of the protrusions 135 and the receiving holes. The plurality of holes in the secondary forming surfaces 151 could come from a roll with holes that meshes with the protrusions 135 while forming surface 130 and the secondary roller rotate in opposite directions at the same surface speed. Alternatively, the plurality of holes in the secondary forming surfaces 151 could come from a surface that would contact yet conform to the protrusions 135 and laminate web 10 while providing enough stiffness to help form the apertures 25 over the protrusions 135. Examples of conforming surfaces on the secondary forming surfaces 151 include brush rollers and felt rollers. In another aspect of improving the formation of apertures 25 in the laminate web 10, one or more of the projection fluid jets emanating from the fluid entangling devices 140c, 140d and 140e may be positioned in relation to the projection forming surface 130 in such a way so as to focus or direct entangling fluid 142 against the protrusions 135 on forming surface 130. By focusing the projection fluid jets in the areas where the laminate web 10 encounters the protrusions 135 on the forming surface 130, a higher flow of entangling fluid 142 serves to better entangle and push the fibers of the laminate web 10 over and around the protrusions 135 to form the apertures 25. The higher (or more focused) flow of entangling fluid 142 results in better entanglement of fibers from the support layer 14 and the projection web 16 around the circumference/perimeter of the aperture 25. Another benefit of focusing the fluid entangling devices on the protrusions 135 is to reduce damage to the land area 19 and projections 12 in the portions of the laminate web 10 not having apertures 25. Each of these process and apparatus aspects for improving the formation of apertures 25 in the laminate web 10 may be used with any one of the configurations illustrated in FIGS. 3, 4, 4A, 5, 6 and 7.

Figure 4A:
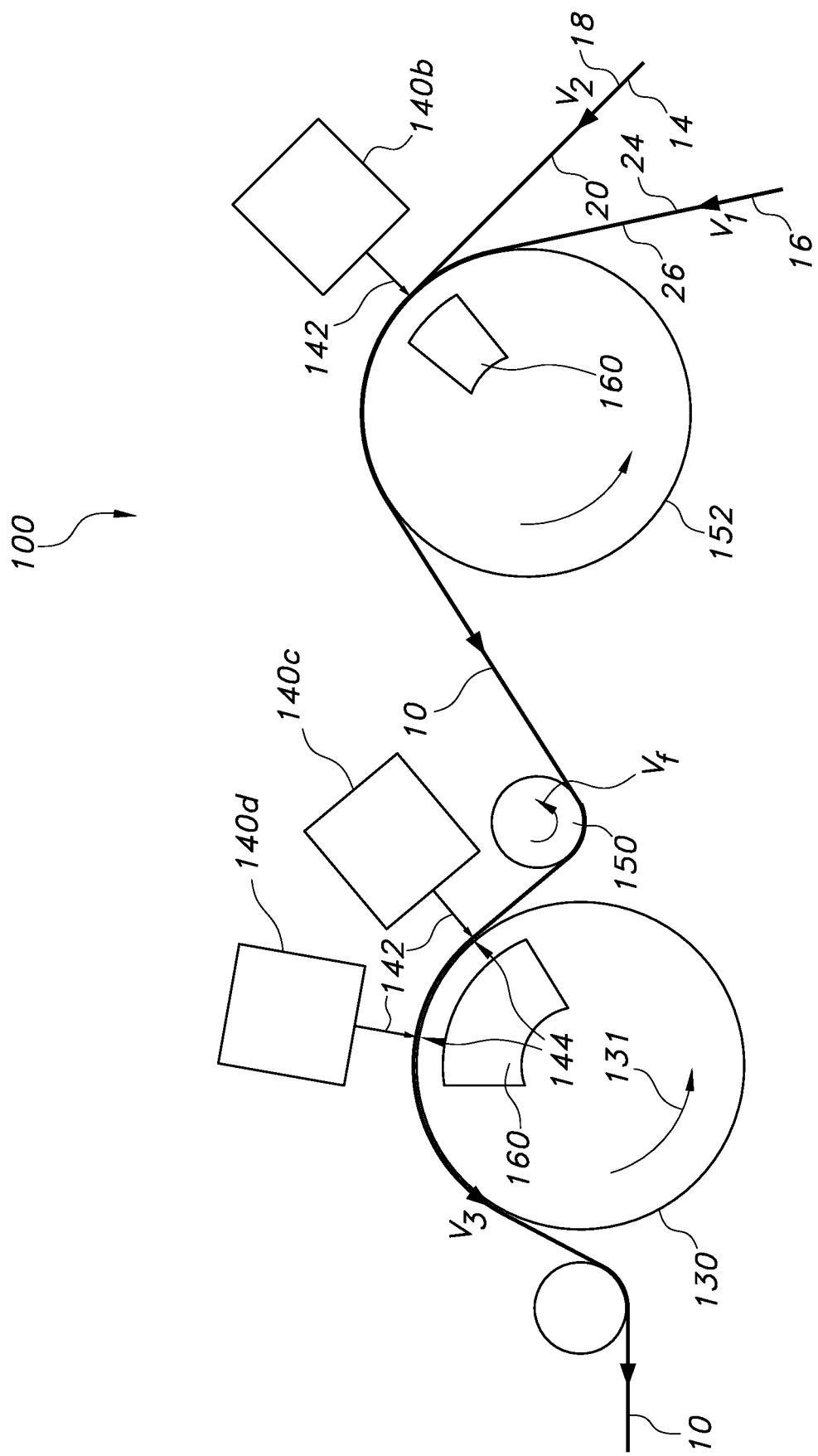
FIG. 4A is a schematic side view of an alternate apparatus and process according to the present invention for forming a fluid-entangled laminate web according to the present invention which is an adaptation of the apparatus and process shown in FIG. 4 as well as subsequent FIGS. 5 and 7.

A further modification of the process and apparatus 100 of FIG. 4 is shown in FIG. 4A. In FIG. 4, as well as subsequent embodiments of the apparatus and process shown in FIGS. 5 and 7, the fluid-entangled laminate web 10 is subjected to a pre-lamination step by way of the lamination forming surface 152 and a lamination fluid entangling device or devices 140*b*. In each of these configurations (FIGS. 4, 5 and 7), the material that is in direct contact with the lamination forming surface 152 is the first surface 18 of support layer 14. However, it is also possible to invert the support layer 14 and the projection web 16 such as is shown in FIG. 4A such that the outer surface 26 of the projection web 16 is the side that is in direct contact with the lamination forming surface 152 and this alternate version of the apparatus and process of FIGS. 4, 5 and 7 is also within the scope of the present invention as well as variations thereof.

Figure 5:
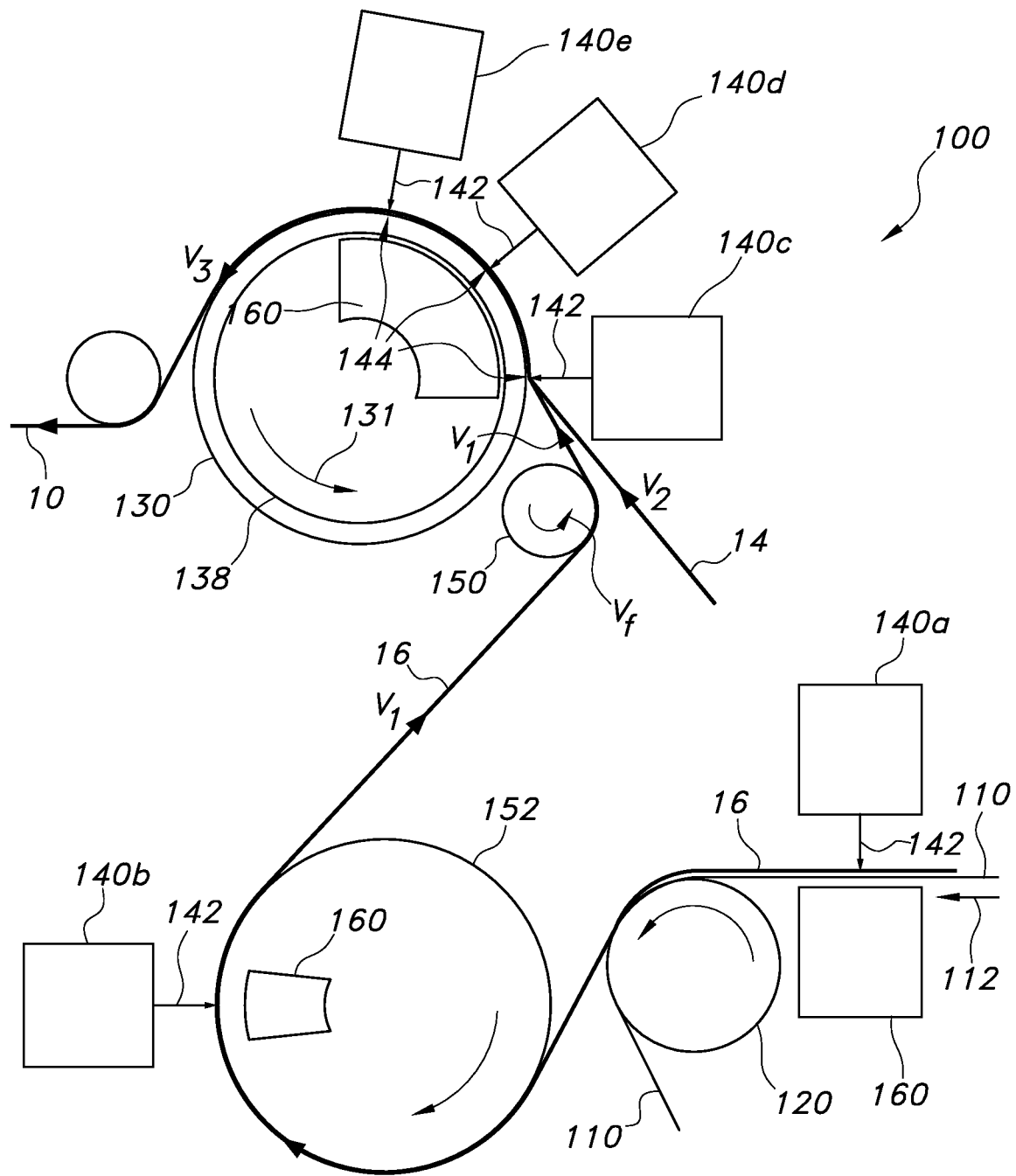
FIG. 5 is a schematic side view of an alternate apparatus and process according to the present invention for forming a fluid-entangled laminate web according to the present invention.

Yet another alternate embodiment of the process and apparatus 100 according to the present invention is shown in FIG. 5. This embodiment is similar to that shown in FIG. 4 except that only the projection web 16 is subjected to pre-entanglement using the fluid entangling devices 140*a* and 140*b* prior to the projection web 16 being fed into the projection forming portion of the equipment. In addition, the support layer 14 is fed into the texturizing zone 144 on the projection forming surface/drum 130 in the same manner as in FIG. 3 though the texturizing zone 144 is supplied with multiple projection fluid entangling devices (140*c*, 140*d* and 140*e*).

Figure 6:
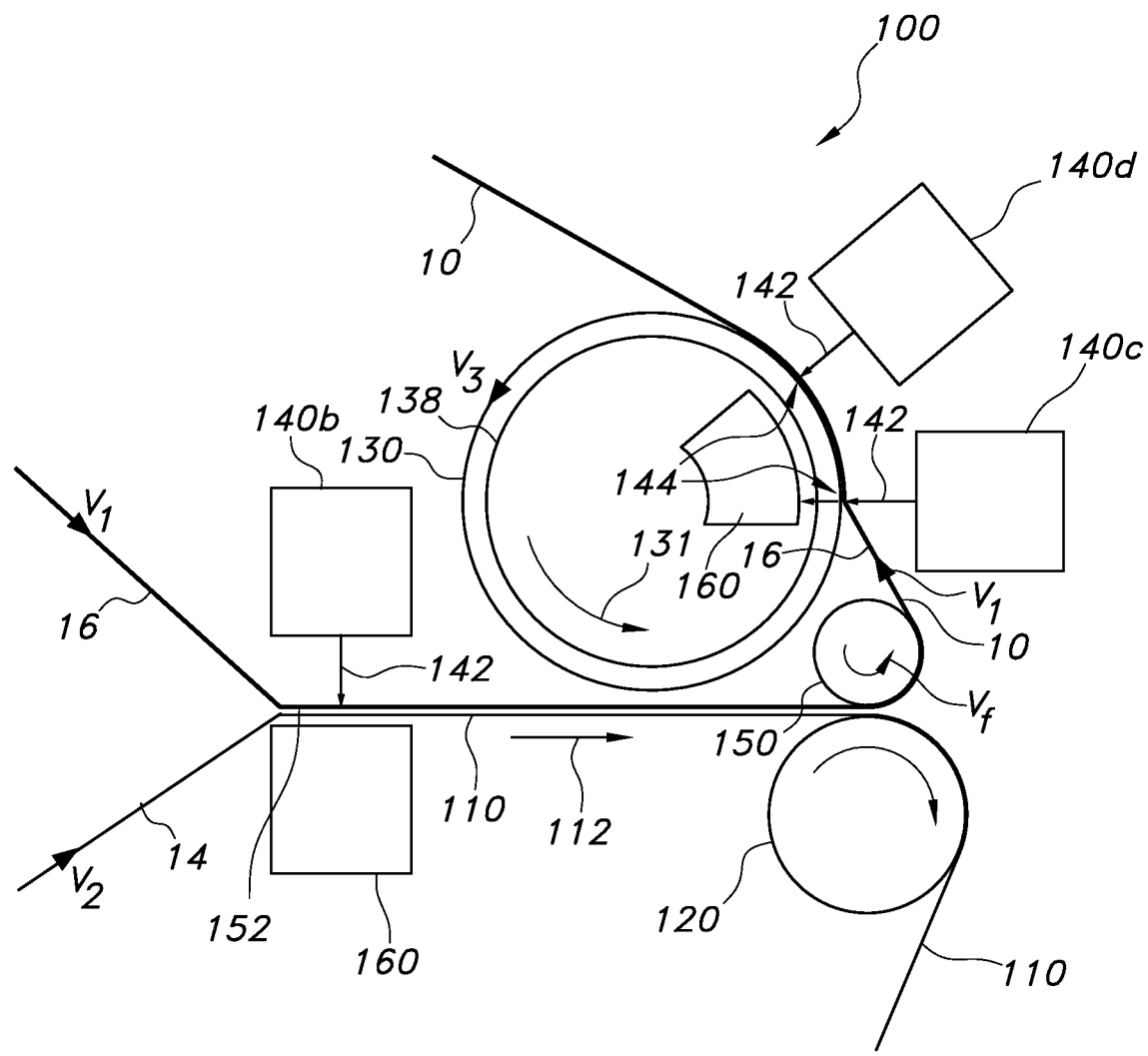
FIG. 6 is a schematic side view of an alternate apparatus and process according to the present invention for forming a fluid-entangled laminate web according to the present invention.

FIG. 6 depicts a further embodiment of the process and apparatus according to the present invention which, like FIG. 4, brings the projection web 16 and the support layer 14 into contact with one another for a lamination treatment in a lamination portion of the equipment and process utilizing a lamination forming surface 152 (which is the same element as the transport belt 110) and a lamination fluid entanglement device 140*b*. In addition, like the embodiment of FIG. 4, in the texturizing zone 144 of the projection forming portion of the process and apparatus 100, multiple projection fluid entangling devices (140*c* and 140*d*) are used.

Figure 7:
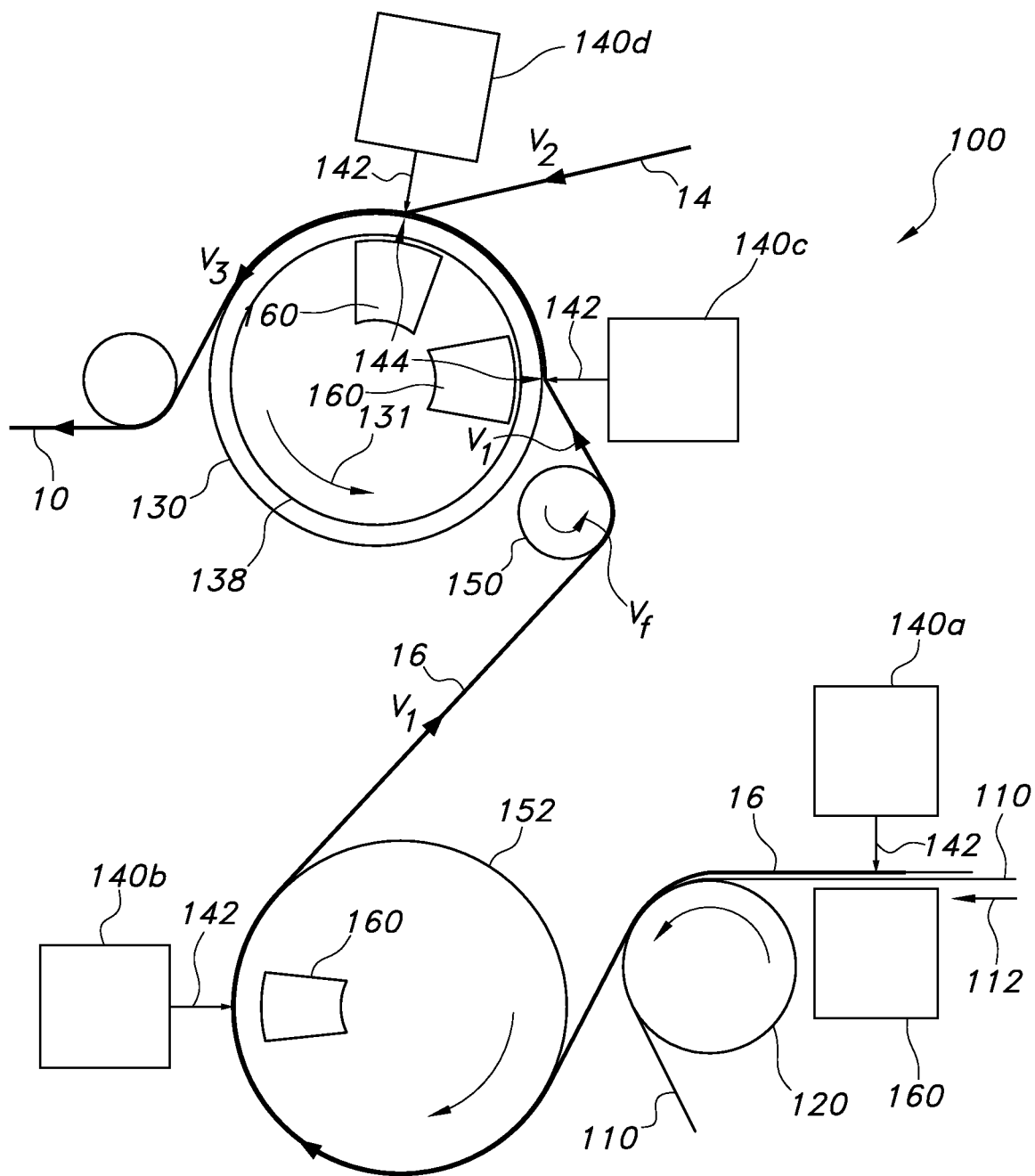
FIG. 7 is a schematic side view of an alternate apparatus and process according to the present invention for forming a fluid-entangled laminate web according to the present invention.

FIG. 7 depicts a further embodiment of the process and apparatus 100 according to the present invention. In FIG. 7, the primary difference is that the projection web 16 undergoes a first treatment with entangling fluid 142 via a projection fluid entangling device 140*c* in the texturizing zone 144 before the second surface 20 of the support layer 14 is brought into contact with the inner surface 24 of the projection web 16 for fluid entanglement via the projection fluid entangling device 140*d*. In this manner, an initial formation of the projections 12 begins without the support layer 14 being in place. As a result, it may be desirable that the projection fluid entangling device 140*c* be operated at a lower pressure than the projection fluid entangling device 140*d*. For example, the projection fluid entangling device 140*c* may be operated in a pressure range of about 100 to about 140 bar whereas the projection fluid entangling device 140*d* may be operated in a pressure range of about 140 to about 200 bar. Other combinations and ranges of pressures can be chosen depending upon the operating conditions of the equipment and the types and basis weights of the materials being used for the projection web 16 and the support layer 14.

In each of the embodiments of the process and apparatus 100, the fibers in the projection web 16 are sufficiently detached and mobile within the projection web 16 such that the entangling fluid 142 emanating from the projection fluid jets in the texturizing zone 144 is able to move a sufficient number of the fibers out of the X-Y plane of the projection web 16 in the vicinity of the forming holes 134 in the projection forming surface 130 and force the fibers down into the forming holes 134 thereby forming the hollow projections 12 in the projection web 16 of the fluid-entangled laminate web 10. Further, the fibers in both the projection web 16 and the support layer 14 are sufficiently detached and mobile such that the entangling fluid 142 and presence of a secondary forming surface 151 force the fibers over and around the protrusions 135 to form apertures 25 in the laminate web 10. In addition, by overfeeding at least the projection web 16 into the texturizing zone 144, enhanced projection formation can be achieved.

Laminate webs 10 formed using the processes and apparatus of the present invention may be used as components in disposable absorbent articles. Disposable absorbent articles can have at least one layer, all or a portion of which, comprises the fluid entangled laminate web of the present invention. These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged either in whole or in part. Furthermore, those of ordinary skill in the art will appreciate that the foregoing description is by way of example only, and is not intended to limit the invention so further described in the appended claims.

What is claimed is:

1. A process for forming a fluid-entangled laminate web having projections comprising the steps of:
   (i) providing a projection forming surface defining a plurality of forming holes therein, said forming holes being spaced apart from one another and having land areas therebetween; said projection forming surface further defining a plurality of protrusions, said protrusions having an adjacent land area; said projection forming surface being capable of movement in a machine direction at a projection forming surface speed;
   (ii) providing a projection fluid entangling device having a plurality of projection fluid jets capable of emitting a plurality of pressurized projection fluid streams of entangling fluid from said plurality of projection fluid jets in a direction towards said projection forming surface;
   (iii) providing a support layer, said support layer having a first surface and an opposed second surface;
   (iv) providing a nonwoven projection web comprising fibers, said projection web having an opposed inner surface and an outer surface;
   (v) feeding said projection web onto said projection forming surface with said outer surface of said projection web positioned adjacent said projection forming surface;
   (vi) feeding said opposed second surface of said support layer onto said inner surface of said projection web;

(vii) directing said plurality of pressurized projection fluid streams of said entangling fluid from said plurality of projection fluid jets in a direction from said first surface of said support layer towards said projection forming surface to cause a) a first plurality of said fibers in said projection web in a vicinity of said forming holes in said projection forming surface to be directed into said forming holes to form a plurality of projections extending outwardly from said outer surface of said projection web, b) formation of apertures through said support layer and said projection web at contact points with said protrusions; and c) a second plurality of said fibers in said projection web to become entangled with said support layer to form a laminate web;

(viii) providing a secondary forming surface located between two of said projection fluid jets after directing said plurality of pressurized projection fluid streams wherein said laminate web passes between said projection forming surface and said secondary forming surface, the secondary forming surface including a plurality of receiving holes positioned to engage with said protrusions of said projection forming surface; and (ix) removing said laminate web from said projection forming surface, wherein at least one of said projection fluid jets is positioned in relation to said projection forming surface to focus said entangling fluid against said protrusions of said projection forming surface.

2. The process of claim 1 wherein fibers of said projection web become entangled with fibers of said support layer along circumferences of said apertures.

3. The process of claim 1 wherein said protrusions have a contact shape selected from pointed, domed and flat.

4. The process of claim 1 wherein said projection forming surface comprises a texturizing drum.

5. The process of claim 4 wherein said land areas of said projection forming surface are not fluid permeable to said entangling fluid.

6. The process of claim 1 wherein said direction of said plurality pressurized projection fluid streams causes the formation of projections which are hollow.

7. The process of claim 1 wherein said projection web is fed onto said projection forming surface at a speed that is greater than a speed said support layer is fed onto said projection web.

8. The process of claim 1 wherein said projection web is fed onto said projection forming surface at an overfeed ratio of between about 10 and about 50 percent.

9. The process of claim 1 wherein said support layer and said projection web are fed onto said projection forming surface at a speed that is greater than said projection forming surface speed.

10. A process for forming a fluid-entangled laminate web having hollow projections comprising the steps of:

(i) providing a lamination forming surface which is permeable to fluids, said lamination forming surface being capable of movement in a machine direction at a lamination forming surface speed;

(ii) providing a projection forming surface defining a plurality of forming holes therein, said forming holes being spaced apart from one another and having land areas therebetween; said projection forming surface further defining a plurality of protrusions, said protrusions having an adjacent land area; said projection forming surface being capable of movement in a machine direction at a projection forming surface speed;

(iii) providing a lamination fluid entangling device having a plurality of lamination fluid jets capable of emitting a plurality of pressurized lamination fluid streams of an entangling fluid from said lamination fluid jets in a direction towards said lamination forming surface;

(iv) providing a projection fluid entangling device having a plurality of projection fluid jets capable of emitting a plurality of pressurized projection fluid streams of an entangling fluid from said projection fluid jets in a direction towards said projection forming surface, (v) providing a support layer, said support layer having an opposed first surface and a second surface;

(vi) providing a nonwoven projection web comprising fibers, said projection web having an opposed inner surface and an outer surface;

(vii) feeding said support layer and said projection web onto said lamination forming surface;

(viii) directing said plurality of pressurized lamination fluid streams from said plurality of lamination fluid jets into said support layer and said projection web to cause at least a portion of said fibers from said projection web to become entangled with said support layer to form a laminate web;

(ix) feeding said laminate web onto said projection forming surface with said outer surface of said projection web adjacent said projection forming surface;

(x) directing said plurality of pressurized projection fluid streams of said entangling fluid from said plurality of projection fluid jets into said laminate web in a direction from said first surface of said support layer towards said projection forming surface to cause a first plurality of said fibers in said projection web in a vicinity of said forming holes in said projection forming surface to be directed into said forming holes to form a plurality of projections extending outwardly from said outer surface of said projection web and to cause formation of apertures through said laminate web at contact points with said protrusions;

(xi) removing said laminate web from said projection forming surface; and providing a secondary forming surface located between two of said projection fluid jets between step (x) and the step of removing said laminate web wherein said laminate web passes between said projection forming surface and said secondary forming surface, wherein said secondary forming surface includes a plurality of receiving holes positioned to engage with said protrusions of said projection forming surface.

11. The process of claim 10 wherein fibers of said laminate web become entangled with each other to a greater degree along circumferences of said apertures.

12. The process of claim 10 wherein said protrusions have a contact shape selected from pointed, domed and flat.

13. The process of claim 10 wherein at least one of said projection fluid jets is positioned in relation to said projection forming surface to focus said entangling fluid against said protrusions of said projection forming surface.

14. The process of claim 10 wherein said projection web is fed onto said support layer at a speed that is greater than a speed said support layer is fed onto said lamination forming surface.

15. The process of claim 14 wherein said laminate is fed onto said projection forming surface at a speed that is greater than said projection forming surface speed.

16. The process of claim 1, wherein multiple of said plurality of projection fluid jets are positioned in relation to said projection forming surface to focus said entangling fluid against said protrusions in contact with said projection web.

17. The process of claim 1, wherein the plurality of projection fluid jets are positioned in relation to said projection forming surface to focus said entangling fluid against each of said protrusions in contact with said projection web.

18. The process of claim 10, wherein at least one of said plurality of projection fluid jets are positioned to direct a pressurized projection fluid stream against one of said plurality of protrusions in contact with said projection web.

19. The process of claim 10, wherein the plurality of projection fluid jets are positioned to direct pressurized projection fluid streams against each of said protrusions in contact with said projection web.

* * * * *